US010336678B2

(12) United States Patent
Shockley et al.

(10) Patent No.: US 10,336,678 B2
(45) Date of Patent: Jul. 2, 2019

(54) COMPOSITIONS AND METHODS FOR PREPARING β,γ-UNSATURATED ACIDS

(71) Applicant: California Institute of Technology, Pasadena, CA (US)

(72) Inventors: Samantha E. Shockley, Pasadena, CA (US); John C. Hethcox, Pasadena, CA (US); Brian M. Stoltz, San Marino, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 15/977,638

(22) Filed: May 11, 2018

(65) Prior Publication Data

US 2018/0327343 A1    Nov. 15, 2018

Related U.S. Application Data

(60) Provisional application No. 62/505,738, filed on May 12, 2017.

(51) Int. Cl.

| | |
|---|---|
| C07C 51/08 | (2006.01) |
| C07C 57/03 | (2006.01) |
| C07C 67/22 | (2006.01) |
| C07C 69/52 | (2006.01) |
| C07C 233/09 | (2006.01) |
| B01J 31/12 | (2006.01) |
| B01J 31/18 | (2006.01) |
| C07C 231/18 | (2006.01) |
| C07C 201/12 | (2006.01) |
| C07C 253/30 | (2006.01) |
| C07C 67/00 | (2006.01) |

(52) U.S. Cl.
CPC .............. *C07C 51/08* (2013.01); *B01J 31/12* (2013.01); *B01J 31/186* (2013.01); *C07C 57/03* (2013.01); *C07C 67/00* (2013.01); *C07C 67/22* (2013.01); *C07C 69/52* (2013.01); *C07C 201/12* (2013.01); *C07C 231/18* (2013.01); *C07C 233/09* (2013.01); *C07C 253/30* (2013.01); *B01J 2231/44* (2013.01); *B01J 2531/827* (2013.01); *C07B 2200/07* (2013.01); *C07C 2601/14* (2017.05); *C07C 2601/16* (2017.05)

(58) Field of Classification Search
CPC ... C07C 231/18; C07C 233/09; C07C 201/12; C07C 253/30; C07C 205/57; C07C 255/38; C07C 51/08; C07C 57/03; C07C 67/22; C07C 69/52; B01J 2231/44; B01J 2531/827; B01J 31/12; B01J 31/186; C07B 2200/07
See application file for complete search history.

(56) References Cited

PUBLICATIONS

Onodera et al. (Iridium-Catalyzed Enantioselective Allylic Alkylation using Chiral Phosphoramidite Ligand Bearing an Amide Moiety, Adv. Synth. Catal., 350, 2725-2732 2008) (Year: 2008).*
Hethcox, J. Caleb; Shockley, Samantha E.; Stoltz, Brian M. "Enantioselective Iridium-Catalyzed Allylic Alkylation Reactions of Masked Acyl Cyanide Equivalents". Organic letters, 2017, 19.7: 1527-1529 Publication Date (Web): Mar. 14, 2017 (Year: 2017).*
Hethcox et al., "Enantioselective Iridium-Catalyzed Allylic Alkylation Reactions of Masked Acyl Cyanide Equivalents," Org Lett, 19(7): 1527-1529 (2017).
Hethcox et al., "Enantioselective Synthesis of Vicinal All-Carbon Quaternary Centers via Iridium-Catalyzed Allylic Alkylation," Angew Chem-Ger Edit 130(28): 8800-8803 (2018).
Hethcox et al., "Iridium-Catalyzed Stereoselective Allylic Alkylation Reactions with Crotyl Chloride," Angew Chem-Ger Edit, 55(52): 16092-16095 (2016).
International Search Report and Written Opinion for International Application No. PCT/US2018/032333 dated Jul. 25, 2018.
Liu et al., "Catalytic Enantioselective Construction of Quaternary Stereocenters: Assembly of Key Building Blocks for the Synthesis of Biologically Active Molecules," Accounts Chem Res, 48(3): 740-751 (2015).
Liu et al., "Construction of Vicinal Tertiary and All-Carbon Quaternary Stereocenters via Ir-Catalyzed Regio-, Diastereo-, and Enantioselective Allylic Alkylation and Applications in Sequential Pd Catalysis," J Am Chem Soc, 135(29): 10626-10629 (2013).
Liu et al., "Enantioselective Gama-Alkylation of Alfa, Beta-Unsaturated Malonates and Ketoesters by a Sequential Ir-Catalyzed Asymmetric Allylic Alkylation/Cope Rearrangement," J Am Chem Soc, 138(16): 5234-5237 (2016).
Nemoto et al., "A Highly Efficient Carbon-Carbon Bond Formation Reaction via Nucleophilic Addition to N-Alkylaldimines without Acids or Metallic Species," J Am Chem Soc, 127: 14546-14547 (2005).
Nemoto et al., "A Three-Step Preparation of MAC Reagents from Malononitrile," Tetrahedron Letters, 44: 73-75 (2003).
Nemoto et al., "Development of a New Acyl Anion Equivalent for the Preparation of Masked Activated Esters and Their Use to Prepare a Dipeptide," J Org Chem, 55: 4515-4516 (1990).
Nemoto et al., "One-Portion Synthesis of 2-Acetoxy Carbonyl Compounds from Aldehydes by Using an Acetylated Masked Acyl Cyanide," Synthesis, 10: 1694-1702 (2009).
Nemoto et al., "Synthesis of α-Amino Acid Precursos Directly from Aldehydes Using Masked Acyl Cyanide Reagents and N,O-Dialkylated Hydroxylamines," J Org Chem, 71: 6038-6043 (2006).
Shockley et al., "Enantioselective Synthesis of Acyclic Alfa-Quaternary Carboxylic Acid Derivatives through Iridium-Catalyzed Allylic Alkylation," Angew Chem-Ger Edit, 129(38): 11703-11706 (2017).

* cited by examiner

*Primary Examiner* — Yevgeny Valenrod
*Assistant Examiner* — Blaine G Doletski
(74) *Attorney, Agent, or Firm* — Foley Hoag LLP

(57) ABSTRACT

The present disclosure provides methods for enantioselective synthesis of acyclic α-quaternary carboxylic acid derivatives via iridium-catalyzed allylic alkylation.

23 Claims, 1 Drawing Sheet

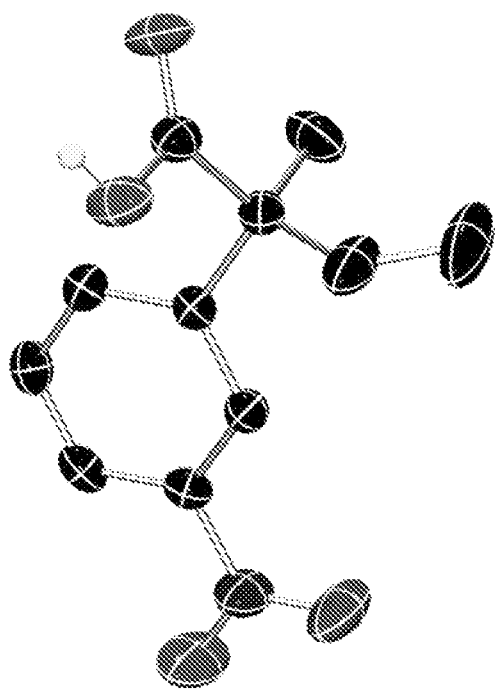

COMPOSITIONS AND METHODS FOR PREPARING β,γ-UNSATURATED ACIDS

RELATED APPLICATIONS

This Application claims the benefit of U.S. Provisional Application 62/505,738, filed May 12, 2017, the contents of which are hereby incorporated herein by reference.

GOVERNMENT SUPPORT

This invention was made with government support under Grant Nos. GM120804 and GM080269 awarded by the National Institutes of Health. The Government has certain rights in the invention.

BACKGROUND

The catalytic enantioselective construction of all-carbon quaternary centers represents a considerable challenge in synthetic organic chemistry due to the difficulties associated with effecting an enantioselective C—C bond formation in a sterically hindered environment.

Synthetic methods for the generation of enantioenriched quaternary stereocenters are highly desirable given their prevalence as motifs in a wide variety of biologically active molecules of both natural and unnatural origin, and the pharmaceutical industries increasing recognition for the motif's applicability in drug design. Despite their importance, the number of highly enantioselective transformations that construct quaternary stereocenters under mild reaction conditions is limited, especially with respect to acyclic systems.

Accordingly, there is a need to develop new reaction protocols that provide access to acyclic α-quaternary carboxylic acid derivatives (i.e., acids, esters, amides).

SUMMARY OF THE INVENTION

Provided herein are methods for the enantioselective synthesis of acyclic α-quaternary carboxylic acid derivatives via iridium-catalyzed allylic alkylation. Accordingly, in one aspect provided herein are methods for preparing a compound of formula (I):

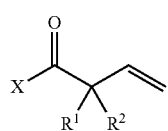

(I)

or a salt thereof,
comprising treating a compound of formula (II):

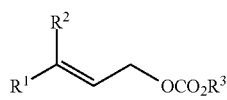

(II)

or a salt thereof,
with a nucleophile and an iridium catalyst under alkylation conditions, wherein, as valence and stability permit, X is OH, OR$^4$, or NR$^a$R$^b$;
R$^1$ and R$^2$ are each independently substituted or unsubstituted alkyl, haloalkyl, alkenyl, alkynyl, aralkyl, cycloalkyl, aryl, heteroaralkyl, heteroaryl, (cycloalkyl)alkyl, cycloalkyl, (heterocycloalkyl)alkyl, or heterocycloalkyl;
R$^3$ is substituted or unsubstituted alkyl, preferably unsubstituted lower alkyl;
R$^4$ is substituted or unsubstituted alkyl, alkenyl, haloalkyl (cycloalkyl)alkyl, or cycloalkyl; and
R$^a$ and R$^b$ are each independently hydrogen or substituted or unsubstituted alkyl, alkenyl, alkynyl, aralkyl, cycloalkyl, aryl, heteroaralkyl, heteroaryl, (cycloalkyl)alkyl, cycloalkyl, (heterocycloalkyl)alkyl, or heterocycloalkyl; or
R$^a$ and R$^b$, together with the nitrogen atom to which they are attached, form a 5- or 6-membered heterocycloalkyl.

Also provided herein are methods for preparing a compound of formula (Ia):

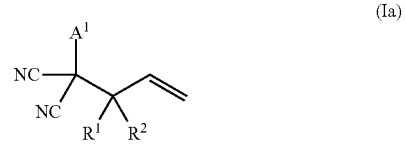

(Ia)

or a salt thereof,
comprising treating a compound of formula (II):

(II)

or a salt thereof,
with a nucleophile and an iridium catalyst under alkylation conditions, wherein, as valence and stability permit,
A$^1$ is —OH or any protecting group, preferably methoxymethyl ether, ethoxymethyl ether, trifluoroethyl ether, benzyl ether, or the like; R$^1$ and Rare each independently substituted or unsubstituted alkyl, haloalkyl, alkenyl, alkynyl, aralkyl, cycloalkyl, aryl, heteroaralkyl, heteroaryl, (cycloalkyl)alkyl, cycloalkyl, (heterocycloalkyl)alkyl, or heterocycloalkyl;
R$^3$ is substituted or unsubstituted alkyl, preferably unsubstituted lower alkyl.

In some embodiments, the nucleophile is a masked acyl cyanide (MAC) nucleophile, having a structure according to formula (A):

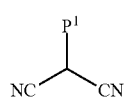

(A)

wherein P$^1$ is any protecting group that is stable to the reaction conditions, such as, for example,

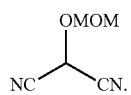

Analogous nucleophiles, e.g., with protecting groups other than methoxymethyl on the oxygen, can be substituted for the depicted MOM ether, for example, ethoxymethyl ethers, trifluoroethyl ethers, benzyl ethers, etc. In short, any protecting group that is stable to the reaction conditions and can be cleaved after the reaction is complete can be used in the subject methods.

In some embodiments, the iridium catalyst is prepared by combining an iridium source, a chiral ligand, and, optionally, a base (e.g., amine, amidine, guanidine base). In preferred embodiments, the iridium source is bis(1,5-cyclooctadiene)diiridium(I) dichloride. Additionally, in some embodiments, the chiral ligand is an enantioenriched phosphorus-based ligand, such as a phosphoramidite ligand.

Also provided herein are methods of synthesizing a pharmaceutical agent by preparing a compound of formula (I) according to a method described herein and synthesizing the pharmaceutical agent from the compound of formula (I).

DETAILED DESCRIPTION OF THE INVENTION

Provided herein are methods for highly enantioselective iridium-catalyzed allylic alkylation, which offer access to products bearing an allylic all-carbon quaternary stereogenic center. In some embodiments, the reaction utilizes a masked acyl cyanide (MAC) reagent, which enables the one-pot preparation of α-quaternary carboxylic acids, esters, and amides with a high degree of enantioselectivity. The allylic alkylation reaction is catalyzed by a robust iridium catalyst and a ligand, preferably a chiral ligand, and the products can be quickly and efficiently elaborated into complex products.

According to some embodiments, a wide range of structurally-diverse, functionalized products are prepared by a readily scalable stereoselective method of iridium-catalyzed enantioselective allylic alkylation. This chemistry is useful in the synthesis of bioactive alkaloids, and for the construction of novel building blocks for medicinal and polymer chemistry.

Indeed, in some embodiments, a method of making a building block compound comprises reacting a substrate compound with a ligand in the presence of an iridium-based catalyst and a solvent. The iridium-based catalysts, ligands, and solvents useful in this reaction are described in more detail below.

Definitions

The definitions for the terms described below are applicable to the use of the term by itself or in combination with another term.

The term "acyl" is art-recognized and refers to a group represented by the general formula hydrocarbyl-C(O)—, preferably alkyl-C(O)—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy, and the like.

The term "alkoxyalkyl" refers to an alkyl group substituted with an alkoxy group, and may be represented by the general formula alkyl-O-alkyl.

The term "alkenyl", as used herein, refers to an aliphatic group containing at least one double bond that is straight chained or branched and has from 1 to about 20 carbon atoms, preferably from 1 to about 10 unless otherwise defined. The term "alkenyl" is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls," the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl such as an alkylC(O)), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a silyl ether, a sulfhydryl, an alkylthio, a sulfate, a sulfonate, a sulfamoyl, a sulfonamido, a sulfonyl, a heterocyclyl, an aralkyl, a heteroaralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthiols, carbonyls (including ketones, aldehydes, carboxylates, and esters), —$CF_3$, —CN, and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_x$-$C_y$" when used in conjunction with a chemical moiety, such as, acyl, acyloxy, alkyl, alkenyl, alkynyl, or alkoxy is meant to include groups that contain from x to y carbons in the chain. For example, the term "$C_x$-$C_y$-alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_2$-$C_y$-alkenyl" and "$C_2$-$C_y$-alkynyl" refer to substituted or unsubstituted unsaturated aliphatic groups analogous in length and possible substitution to the alkyls described above, but that contain at least one double or triple bond respectively.

The term "alkylthio," as used herein, refers to a thiol group substituted with an alkyl group and may be represented by the general formula alkyl-S—.

The term "alkynyl", as used herein, refers to an aliphatic group containing at least one triple bond and is intended to include both "unsubstituted alkynyls" and "substituted alkynyls," the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide," as used herein, refers to a group

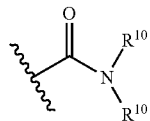

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

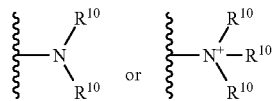

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl," as used herein, refers to an alkyl group substituted with an amino group.

The term "aralkyl," as used herein, refers to an alkyl group substituted with an aryl group. An aralkyl group is connected to the rest of the molecule through the alkyl component of the aralkyl group.

The term "aryl" as used herein include substituted or unsubstituted single-ring aromatic groups in which each atom of the ring is carbon. Preferably, the ring is a 5- to 10-membered ring, more preferably a 6- to 10-membered ring or a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like. Exemplary substitution on an aryl group can include, for example, a halogen, a haloalkyl such as trifluoromethyl, a hydroxyl, a carbonyl (such as a carboxyl, an alkoxycarbonyl, a formyl, or an acyl such as an alkylC(O)), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a silyl ether, a sulfhydryl, an alkylthio, a sulfate, a sulfonate, a sulfamoyl, a sulfonamido, a sulfonyl, a heterocyclyl, an aralkyl, or an aromatic or heteroaromatic moiety The terms "carbocycle" and "carbocyclic," as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene, and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two, three, or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbonate" is art-recognized and refers to a group —$OCO_2$—$R^{10}$, wherein $R^{10}$ represents a hydrocarbyl group.

The term "carboxyl", as used herein, refers to a group represented by the formula —$CO_2H$.

The term "ester," as used herein, refers to a group —$C(O)OR^{10}$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl," as used herein, refers to an alkyl group substituted with a heteroaryl group.

The term "heteroalkyl," as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include 5- to 10-membered cyclic or polycyclic ring systems, including, for example, pyrrole, furan, thiophene, imidazole, oxazole, thiazole, pyrazole, pyridine, pyrazine, pyridazine, and pyrimidine, and the like. Exemplary optional substituents on heteroaryl groups include those substituents put forth as exemplary substituents on aryl groups, above.

The term "heteroatom" as used herein means an atom of any element other than carbon or hydrogen. Preferred heteroatoms are nitrogen, oxygen, and sulfur.

The terms "heterocycloalkyl," "heterocycle," and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocycloalkyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocycloalkyls. Heterocycloalkyl groups include, for example, piperidine, piperazine, pyrrolidine, morpholine, lactones, lactams, and the like.

The term "hydrocarbyl," as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl," as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl," for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a haloalkyl, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonate" is art-recognized and refers to the group SO$_3$H, or a pharmaceutically acceptable salt thereof. In some embodiments, a sulfonate can mean an alkylated sulfonate of the formula SO$_3$(alkyl).

The term "thioester", as used herein, refers to a group —C(O)SR$^{10}$ or —SC(O)R$^{10}$ wherein R$^{10}$ represents a hydrocarbyl.

Methods of the Invention

Provided herein are methods for preparing a compound of formula (I):

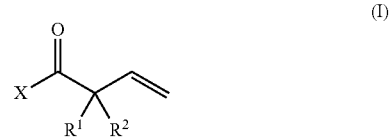

or a salt thereof, comprising treating a compound of formula (II):

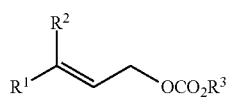

(II)

or a salt thereof,
with a nucleophile and an iridium catalyst under alkylation conditions, wherein, as valence and stability permit,
X is OH, OR$^4$, or NR$^a$R$^b$;
R$^1$ and R$^2$ are each independently substituted or unsubstituted alkyl, haloalkyl, alkenyl, alkynyl, aralkyl, cycloalkyl, aryl, heteroaralkyl, heteroaryl, (cycloalkyl)alkyl, cycloalkyl, (heterocycloalkyl)alkyl, or heterocycloalkyl;
R$^3$ is substituted or unsubstituted alkyl, preferably unsubstituted lower alkyl;
R$^4$ is substituted or unsubstituted alkyl, alkenyl, haloalkyl (cycloalkyl)alkyl, or cycloalkyl; and
R$^a$ and R$^b$ are each independently hydrogen or substituted or unsubstituted alkyl, alkenyl, alkynyl, aralkyl, cycloalkyl, aryl, heteroaralkyl, heteroaryl, (cycloalkyl)alkyl, cycloalkyl, (heterocycloalkyl)alkyl, or heterocycloalkyl; or
R$^a$ and R$^b$, together with the nitrogen atom to which they are attached, form a 5- or 6-membered heterocycloalkyl.

In some embodiments, the compound of formula (I) is enantioenriched. For example, in certain embodiments, the compound of formula (I) has about 70% ee or greater, about 80% ee or greater, about 85% ee or greater, about 88% ee or greater, about 90% ee or greater, about 91% ee or greater, about 92% ee or greater, about 93% ee or greater, about 94% ee or greater, about 95% ee or greater, about 96% ee or greater, about 97% ee or greater, about 98% ee or greater, or about 99% ee or greater.

Also provided herein are methods for the preparation of the compound of formula (Ia):

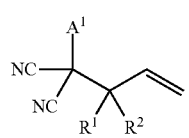

(Ia)

or a salt thereof,
comprising treating a compound of formula (II):

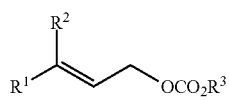

(II)

or a salt thereof;
with a nucleophile and an iridium catalyst under alkylation conditions, wherein, as valence and stability permit,
A$^1$ is —OH or any protecting group, preferably methoxymethyl ether, ethoxymethyl ether, trifluoroethyl ether, benzyl ether, or the like;
R$^1$ and R$^2$ are each independently substituted or unsubstituted alkyl, haloalkyl, alkenyl, alkynyl, aralkyl, cycloalkyl, aryl, heteroaralkyl, heteroaryl, (cycloalkyl)alkyl, cycloalkyl, (heterocycloalkyl)alkyl, or heterocycloalkyl;
R$^3$ is substituted or unsubstituted alkyl, preferably unsubstituted lower alkyl;
R$^4$ is substituted or unsubstituted alkyl, alkenyl, haloalkyl (cycloalkyl)alkyl, or cycloalkyl.

In some embodiments, the compound of formula (Ia) is enantioenriched. For example, in certain embodiments, the compound of formula (Ia) has about 70% ee or greater, about 80% ee or greater, about 85% ee or greater, about 88% ee or greater, about 90% ee or greater, about 91% ee or greater, about 92% ee or greater, about 93% ee or greater, about 94% ee or greater, about 95% ee or greater, about 96% ee or greater, about 97% ee or greater, about 98% ee or greater, or about 99% ee or greater.

In certain embodiments, the methods provided herein comprise treating the compound of formula (Ia) with acid in the presence of water to provide the compound of formula (I):

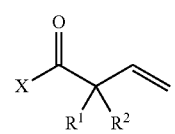

(I)

or salt thereof,
wherein X is OH.

In some such embodiments, the acid can be any suitable organic or inorganic acid, including but not limited to, hydrochloric acid, hydrobromic acid, hydroiodic acid, sulfuric acid, nitric acid, phosphoric acid, acetic acid, trifluoroacetic acid, trifluoromethanesulfonic acid, p-toluenesulfonic acid, and/or aminomethylphosphonic acid. In preferred embodiments, the acid is hydrochloric acid.

In other embodiments, the methods provided herein comprise treating the compound of formula (Ia) with an alcohol to provide a compound of formula (I):

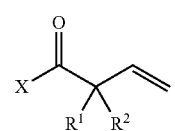

(I)

or salt thereof,
wherein X is OR$^4$; and
R$^4$ is substituted or unsubstituted alkyl, alkenyl, haloalkyl, (cycloalkyl)alkyl, or cycloalkyl.

In yet other embodiments, the methods provided herein comprise treating the compound of formula (Ia) with an amine to provide a compound of formula (I):

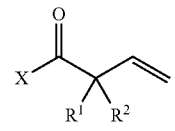

(I)

or salt thereof, wherein X is NR$^a$R$^b$; and

R$^a$ and R$^b$ are each independently hydrogen or substituted or unsubstituted alkyl, alkenyl, alkynyl, aralkyl, cycloalkyl, aryl, heteroaralkyl, heteroaryl, (cycloalkyl)alkyl, cycloalkyl, (heterocycloalkyl)alkyl, or heterocycloalkyl; or R$^a$ and R$^b$, together with the nitrogen atom to which they are attached, form a substituted or unsubstituted 5- or 6-membered heterocycloalkyl.

In some embodiments, R$^1$ and R$^2$ are each independently substituted or unsubstituted alkyl or aryl. In some such embodiments, R$^1$ is substituted or unsubstituted aryl; and R$^2$ is substituted or unsubstituted alkyl. In certain embodiments, R$^1$ is unsubstituted aryl (e.g., phenyl). In certain other embodiments, R$^2$ is C$_1$-C$_4$-alkyl (e.g., methyl). Where R$^1$ and/or R$^2$ are substituted aryl (e.g., phenyl), exemplary substitutes include, but are not limited to, one or more of nitro, halogen (e.g., fluoro, chloro, bromo), lower alkyl (e.g., methyl), hydroxyalkyl (e.g., CH$_2$OH), and/or haloalkyl (e.g., CF$_3$).

Masked Acyl Cyanide (MAC) Nucleophiles

In some embodiments, the nucleophile is a masked acyl cyanide (MAC) nucleophile. MAC nucleophiles are reverse-polarity nucleophiles. Following reaction with an electrophile, these umpoled synthons can be unmasked to reveal a transient acyl cyanide intermediate, which can be further transformed into a carboxylic acid, amide, or ester.

In some embodiments, the MAC nucleophiles used in the disclosed methods have a structure according to formula (A):

wherein P$^1$ is any protecting group that is stable to the reaction conditions. For example, in some embodiments, P$^1$ is methoxymethyl ether, ethoxymethyl ether, trifluoroethyl ether, benzyl ether, and the like. In preferred embodiments, P$^1$ is methoxymethyl ether. That is, in the most preferred embodiments, masked acyl cyanide (MAC) nucleophile is

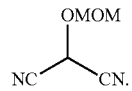

Transition Metal Catalysts

Preferred transition metal catalysts of the invention are complexes of iridium. In some embodiments, the transition metal catalyst is an iridium catalyst.

In some embodiments, the iridium catalyst is prepared by combining an iridium source and a chiral ligand. In preferred embodiments the iridium catalyst is prepared by combining an iridium source, a chiral ligand, and a base (e.g., amine, amidine, guanidine base).

Exemplary iridium sources that may be used in the methods of the invention include, but are not limited to, (acetylacetonato)(1,5-cyclooctadiene)iridium(I), (acetylacetonato)(1,5-cyclooctadiene)iridium(I), (acetylacetonato)di-carbonyliridium(I), bis[1,2-bis(diphenylphosphino)ethane] carbonyl chloroiridium(I), bis(1,5-cyclooctadiene)diiridium (I) dichloride, bis(1,5-cyclooctadiene)iridium(I) tetrafluoroborate, bis(cyclooctadiene)iridium(I) tetrakis(3,5-bis(trifluoromethyl)phenyl)borate, chlorobis(cyclooctene)iridium(I)dimer, (1,5-cyclooctadiene)bis(methyldiphenylphosphine)iridium(I) hexafluorophosphate, (1,5-cyclooctadiene)(hexafluoroacetylacetonato)iridium(I), (1,5-cyclooctadiene)-η5-indenyl)iridium(I), (1,5-cyclooctadiene)(methoxy)iridium(I) dimer, (1,5-cyclooctadiene)(pyridine)(tricyclohexylphosphine)-iridium (I) hexafluorophosphate, (1,5-cyclooctadiene)(pyridine) (tricyclohexylphosphine)-iridium(I) hexafluorophosphate, and (1,5-cyclooctadiene)(pyridine)(tricyclohexylphosphine) iridium(I) tetrakis[3,5-bis(trifluoromethyl)phenyl]borate. In preferred embodiments, the iridium source is bis(1,5-cyclooctadiene)diiridium(I) dichloride.

Accordingly, when describing the amount of transition metal catalyst used in the methods of the invention, the following terminology applies. The amount of transition metal catalyst present in a reaction is alternatively referred to herein as "catalyst loading". Catalyst loading may be expressed as a percentage that is calculated by dividing the moles of catalyst complex by the moles of the substrate present in a given reaction. Catalyst loading is alternatively expressed as a percentage that is calculated by dividing the moles of total transition metal (for example, iridium) by the moles of the substrate present in a given reaction.

In certain embodiments, the transition metal catalyst is present under the conditions of the reaction from an amount of about 0.01 mol % to about 10 mol % total iridium relative to the substrate, which is the compound of formula (II). In certain embodiments, the catalyst loading is from about 0.05 mol % to about 8 mol % total iridium relative to the substrate. In certain embodiments, the catalyst loading is from about 0.05 mol % to about 8 mol %, about 1 mol % to about 8 mol % about 1.5 mol % to about 8 mol % about 2 mol % to about 8 mol %, about 2.5 mol % to about 8 mol %, about 3 mol % to about 8 mol %, about 3.5 mol % to about 8 mol %, about 3.5 mol % to about 7.5 mol %, about 3.5 mol % to about 7 mol %, about 3.5 mol % to 6.5 mol %, about 3.5 mol % to about 6 mol %, about 3.5 mol % to about 5.5 mol %, about 3.5 mol % to about 5 mol %, about 3.5 mol % to about 4.5 mol % total iridium relative to the substrate. In some embodiments, the catalyst loading is from about 0.05 mol % to about 7.5 mol %, about 0.05 mol % to about 7 mol %, about 0.05 mol % to about 6.5 mol %, about 0.05 mol % to about 6 mol %, about 0.05 mol % to about 5.5 mol %, about 0.05 mol % to about 5 mol %, about 0.05 mol % to about 4.5 mol %, or about 0.05 mol % to about 4 mol % total iridium relative to the substrate. In some embodiments, the catalyst loading is from about 1 mol % to about 8 mol %, about 1 mol % to about 7.5 mol %, about 1 mol % to about 7 mol %, about 1 mol % to about 6.5 mol %, about 1 mol % to about 6 mol %, about 1 mol % to about 5.5 mol %, about 1 mol % to about 5 mol %, about 1 mol % to about 4.5 mol %, or about 1 mol % to about 4 mol % total iridium relative to the substrate. In some embodiments, the catalyst loading is from about 1.5 mol % to about 8 mol %, about 1.5 mol % to about 7.5 mol %, about 1.5 mol % to about 7 mol %, about 1.5 mol % to about 6.5 mol %, about 1.5 mol % to about 6 mol %, about 1.5 mol % to about 5.5 mol %, about 1.5 mol % to about 5 mol %, about 1.5 mol % to about 4.5 mol %, or about 1.5 mol % to about 4 mol % total iridium relative to the substrate. In some embodiments, the catalyst loading is from about 2 mol % to about 8 mol %, about 2 mol % to about 7.5 mol %, about 2 mol % to about 7 mol %, about 2 mol % to about 6.5 mol %, about 2 mol % to about 6 mol %, about 2 mol % to about 5.5 mol %, about 2 mol % to about 5 mol %, about 2 mol % to about 4.5 mol %, or about 2 mol % to about 4 mol % total iridium relative to the substrate. In some embodiments, the catalyst loading is from about 2.5 mol % to about 8 mol %, about 2.5 mol % to about 7.5 mol %, about 2.5 mol % to about 7 mol %, about 2.5 mol % to about 6.5 mol %, about 2.5 mol % to about 6 mol %, about 2.5 mol % to about 5.5 mol %, about 2.5 mol % to about 5 mol %, about 2.5 mol % to about 4.5 mol %, or about 2.5 mol % to about 4 mol % total iridium relative to the substrate. In some embodiments, the catalyst loading is from about 3 mol % to about 8 mol %, about 3 mol % to about 7.5 mol %, about 3 mol % to about 7 mol %, about 3 mol % to about 6.5 mol %, about 3 mol % to about 6 mol %, about 3 mol % to about 5.5 mol %, about 3 mol % to about 5 mol %, about 3 mol % to about 4.5 mol %, or about 3 mol % to about 4 mol % total iridium relative to the substrate. In some embodiments, the catalyst loading is from about 3.5 mol % to about 8 mol %, about 3.5 mol % to about 7.5 mol %, about 3.5 mol % to about 7 mol %, about 3.5 mol % to about 6.5 mol %, about 3.5 mol % to about 6 mol %, about 3.5 mol % to about 5.5 mol %, about 3.5 mol % to about 5 mol %, about 3.5 mol % to about 4.5 mol %, or about 3.5 mol % to about 4 mol % total iridium relative to the substrate. For example, in certain embodiments, the catalyst loading is about 0.01 mol %, about 0.05 mol %, about 0.1 mol %, about 0.15 mol %, about 0.2 mol %, about 0.25 mol %, about 0.3 mol %, about 0.4 mol %, about 0.5 mol %, about 0.6 mol %, about 0.7 mol %, about 0.8 mol %, about 0.9 mol %, about 1 mol %, about 1.5 mol %, about 2 mol %, about 3 mol %, or about 5 mol % total iridium. In certain other embodiments, the catalyst loading is about 0.5 mol %, about 0.75 mol %, about 1 mol %, about 1.25 mol %, about 1.5 mol %, about 1.75 mol %, about 2 mol %, about 2.25 mol %, about 2.5 mol %, about 2.75 mol %, about 3 mol %, about 3.25 mol %, about 3.5 mol %, about 3.75 mol %, about 4 mol %, about 4.25 mol %, about 4.5 mol %, about 4.75 mol %, about 5 mol %, about 5.25 mol %, about 5.5 mol %, about 5.75 mol %, about 6 mol %, about 6.25 mol %, about 6.5 mol %, about 6.75 mol %, about 7 mol %, about 7.25 mol %, about 7.5 mol %, about 7.75 mol %, or about 8 mol % total iridium. In preferred embodiments, the catalyst loading is about 4 mol % total iridium.

Chiral Ligands

One aspect of the invention relates to the enantioselectivity of the methods. Enantioselectivity results from the use of chiral ligands during the allylic alkylation reaction. Accordingly, the iridium catalyst comprises a chiral ligand. Without being bound by theory, the asymmetric environment that is created around the metal center by the presence of chiral ligands produces an enantioselective reaction. The chiral ligand forms a complex with the transition metal (i.e., iridium), thereby occupying one or more of the coordination sites on the metal and creating an asymmetric environment around the metal center. This complexation may or may not involve the displacement of achiral ligands already complexed to the metal. When displacement of one or more achiral ligands occurs, the displacement may proceed in a concerted fashion, i.e., with both the achiral ligand decomplexing from the metal and the chiral ligand complexing to the metal in a single step. Alternatively, the displacement may proceed in a stepwise fashion, i.e., with decomplexing of the achiral ligand and complexing of the chiral ligand occurring in distinct steps. Complexation of the chiral ligand to the transition metal may be allowed to occur in situ, i.e., by admixing the ligand and metal before adding the substrate. Alternatively, the ligand-metal complex can be formed separately, and the complex isolated before use in the alkylation reactions of the present invention.

Once coordinated to the transition metal center, the chiral ligand influences the orientation of other molecules as they interact with the transition metal catalyst. Coordination of the metal center with a π-allyl group and reaction of the substrate with the π-allyl-metal complex are dictated by the presence of the chiral ligand. The orientation of the reacting species determines the stereochemistry of the products.

Chiral ligands of the invention may be bidentate or monodentate or, alternatively, ligands with higher denticity (e.g., tridentate, tetradentate, etc.) can be used. In preferred embodiments, the ligand is a bidentate ligand. Additionally, it is preferred that the ligand be substantially enantiopure. By "enantiopure" is meant that only a single enantiomer is present. In many cases, substantially enantiopure ligands (e.g., ee >99%, preferably ee >99.5%, even more preferably ee >99.9%) can be purchased from commercial sources, obtained by successive recrystallizations of an enantioenriched substance, or by other suitable means for separating enantiomers.

Exemplary chiral ligands may be found in U.S. Pat. No. 7,863,443 and CN Patent No. 105524111B, the entireties of which are incorporated herein by reference. In certain embodiments, the chiral ligand is an enantioenriched phosphine ligand. In certain embodiments, the enantioenriched phosphorus-based ligand is a phosphoramidite ligand. Preferred phosphoramidite ligands include:

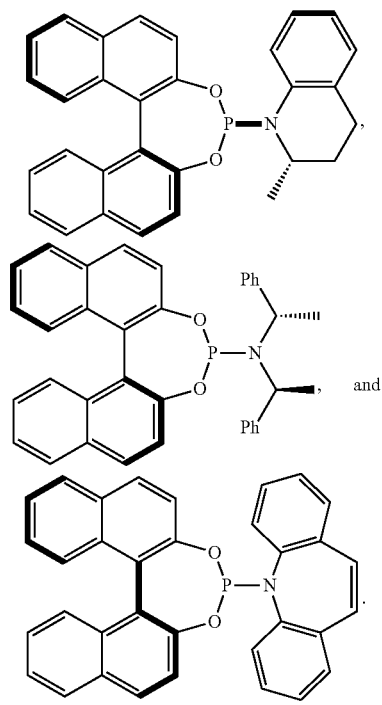

Generally, the chiral ligand is present in an amount in the range of about 1 equivalent to about 20 equivalents relative to the amount of total metal from the catalyst, preferably in the range of about 1 to about 15 equivalents relative to the amount of total metal from the catalyst, and most preferably in the range of about 1 equivalent relative to the amount of total metal from the catalyst. Alternatively, the amount of the chiral ligand can be measured relative to the amount of the substrate.

In certain embodiments, the ligand is present under the conditions of the reaction from an amount of about 0.1 mol % to about 100 mol % relative to the substrate, which is the compound of formula (II). The amount of the chiral ligand present in the reaction is alternatively referred to herein as "ligand loading" and is expressed as a percentage that is calculated by dividing the moles of ligand by the moles of the substrate present in a given reaction. In certain embodiments, the ligand loading is from about 1 mol %, about 1.1 mol %, about 1.2 mol %, about 1.3 mol %, about 1.4 mol %, about 1.5 mol %, about 1.6 mol %, about 1.7 mol %, about 1.8 mol %, about 1.9 mol %, about 2 mol %, about 2.1 mol %, about 2.2 mol %, about 2.3 mol %, about 2.4 mol %, about 2.5 mol %, about 2.6 mol %, about 2.7 mol %, about 2.8 mol %, about 2.9 mol %, about 3 mol %, about 3.1 mol %, about 3.2 mol %, about 3.3 mol %, about 3.4 mol %, about 3.5 mol %, about 3.6 mol %, about 3.7 mol %, about 3.8 mol %, about 3.9 mol %, about 4 mol %, about 4.1 mol %, about 4.2 mol %, about 4.3 mol %, about 4.4 mol %, about 4.5 mol %, about 4.6 mol %, about 4.7 mol %, about 4.8 mol %, about 4.9 mol %, or about 5 mol %. In preferred embodiments, the ligand loading is 2.2 mol %.

Where a chiral ligand is used, the reactions of the invention may enrich the stereocenter bearing $R^1$ and $R^2$ in the product relative to the enrichment at this center, if any, of the starting material. In certain embodiments, the chiral ligand used in the methods of the invention yields a compound of formula (I) that is enantioenriched. The level of enantioenrichment of a compound may be expressed as enantiomeric excess (ee). The ee of a compound may be measured by dividing the difference in the fractions of the enantiomers by the sum of the fractions of the enantiomers. For example, if a compound is found to comprise 98% (S)-enantiomer, and 2% (R) enantiomer, then the ee of the compound is (98−2)/(98+2), or 96%. In certain embodiments, the compound of formula (I) has about 30% ee or greater, about 40% ee or greater, about 50% ee or greater, 60% ee or greater, about 70% ee or greater, about 80% ee or greater, about 85% ee or greater, about 88% ee or greater, about 90% ee or greater, about 91% ee or greater, about 92% ee or greater, about 93% ee or greater, about 94% ee or greater, about 95% ee or greater, about 96% ee or greater, about 97% ee or greater, about 98% ee or greater, or about 99% ee or greater, even where this % ee is greater than the % ee of the starting material, such as 0% ee (racemic).

In certain embodiments, the compound of formula (I) or (Ia) is enantioenriched. In certain embodiments, the compound of formula (I) or (Ia) is enantiopure.

In embodiments where the starting material has more than one stereocenter, reactions of the invention may enrich the stereocenter bearing $R^1$ and $R^2$ relative to the enrichment at this center, if any, of the starting material, and substantially independently of the stereochemical disposition/enrichment of any other stereocenters of the molecule. For example, a product of the methods described herein may have about 30% ee or greater, about 40% ee or greater, about 50% ee or greater, about 60% ee or greater, about 70% ee or greater, about 80% ee or greater, about 90% ee or greater, about 95% ee or greater, about 98% ee or greater, or even about 99% ee or greater at the stereocenter of the product bearing $R^1$ and $R^2$.

Additives

To improve the effectiveness of the catalysts discussed herein, additional reagents (also referred to herein as an additive) may be employed, including, without limitation, acids (e.g., Lewis acids), salts, solvents, and other small molecules. In certain embodiments, the additive is a Lewis acid. Exemplary Lewis acids include, but are not limited to, boron trifluoride diethyletherate, boron trifluoride methyl sulfide complex, boron trichloride methyl sulfide complex, boron trifluoride tert-butyl methyl etherate, boron trifluoride propanol complex, boron trifluoride phenol complex, trimethylborane, triethylborane, tri-n-butylborane, di-n-butylboron triflate, boron trifluoride, boron trichloride, dimethyl aluminum chloride, aluminum bromide, aluminum chloride, or aluminum isopropoxide. In preferred embodiments, the Lewis acid is triethylborane.

In some embodiments, the additive is used in an amount from about 1 mol % to about 1000 mol % relative to the compound of formula (II). In some such embodiments, the additive is used in an amount from about 50 mol % to about 500 mol % relative to the compound of formula (II). In certain embodiments, the additive is used in an amount of about 50 mol %, about 75 mol %, about 100 mol %, about 125 mol %, about 150 mol %, about 175 mol %, about 200 mol %, about 225 mol %, about 250 mol %, about 275 mol %, about 300 mol %, about 325 mol %, about 350 mol %, about 375 mol %, about 400 mol %, about 425 mol %, about 450 mol %, about 475 mol %, or about 500 mol %. In preferred embodiments, the additive is used in an amount of about 200 mol %.

Bases

In some embodiments, the effectiveness of the catalyst may be affected by the addition of a base. Common bases that may be included in the reaction include, but are not limited to, 1,3,5-triazabicyclo[4.4.0]dec-5-ene, 1,8-diazabicyclo[5.4.0]undec-7-ene, and/or n-isopropylamine. In preferred embodiments, the base is 1,3,5-triazabicyclo[4.4.0]dec-5-ene.

In some embodiments, the base is used in an amount from 0.1 mol % to about 100 mol % relative to the compound of formula (II). In some such embodiments, the base is used in an amount from about 0.5 mol % to about 50 mol % relative to the compound of formula (II). In certain embodiments, the base is used in an amount of about 0.5 mol %, about 1 mol %, about 2 mol %, about 3 mol %, about 4 mol %, about 5 mol %, about 6 mol %, about 7 mol %, about 8 mol %, about 9 mol %, about 10 mol %, about 11 mol %, about 12 mol %, about 13 mol %, about 14 mol %, about 15 mol %, about 16 mol %, about 17 mol %, about 18 mol %, about 19 mol %, or about 20 mol %. In preferred embodiments, the base is used in an amount of about 10 mol %.

Alkylation Conditions

In certain embodiments, the methods of the invention include treating a compound of formula (II), with an iridium catalyst under alkylation conditions. In certain embodiments, alkylation conditions of the reaction include one or more organic solvents. In certain embodiments, organic solvents include aromatic or non-aromatic hydrocarbons, ethers, alkylacetates, nitriles, or combinations thereof. In certain embodiments, organic solvents include hexane, pentane, benzene, toluene, xylene, cyclic ethers such as optionally substituted tetrahydrofuran and dioxane, acyclic ethers such as dimethoxyethane, diethyl ether, methyl tert-butyl ether, and cyclopentyl methyl ether, acetonitrile, isobutyl acetate, ethyl acetate, isopropyl acetate, or combinations thereof. In preferred embodiments, the solvent is tetrahydrofuran.

In certain embodiments, alkylation conditions of the reaction include a reaction temperature. In certain embodiments, the reaction temperature is ambient temperature (about 20° C. to about 26° C.). In certain embodiments, the reaction temperature is higher than ambient temperature, such as, for example, about 30° C., about 35° C., about 40° C., about 45° C., about 50° C., about 55° C., or about 60° C. Reaction temperature may be optimized per each substrate.

In certain embodiments, instruments such as a microwave reactor may be used to accelerate the reaction time. Pressures range from atmospheric to pressures typically used in conjunction with supercritical fluids, with the preferred pressure being atmospheric.

Synthesis of Compound Libraries

Diverse, small molecule compound libraries (including salts of compounds) may be generally synthesized according to Scheme 1.

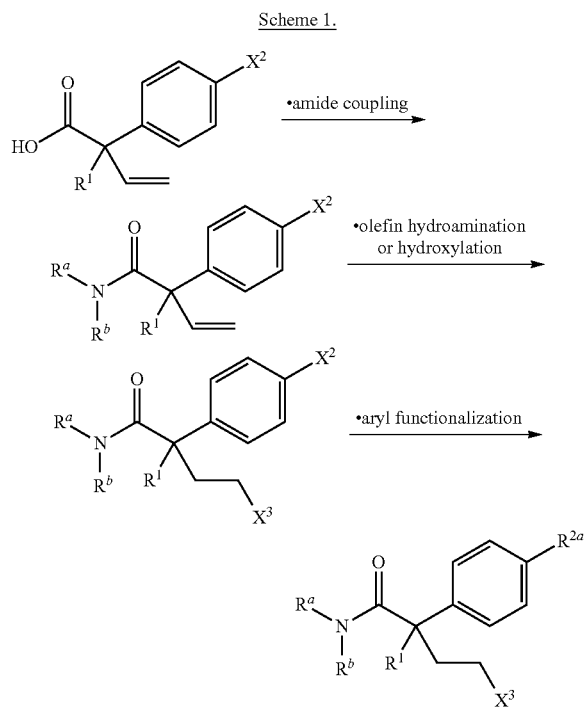

wherein, as valence and stability permit,
$X^2$ is H, Cl, Br, I, OTf, boron moiety, or tin moiety;
$X^3$ is $NR^aR^b$ or $OR^c$;
$R^1$ and $R^2$ are each independently substituted or unsubstituted alkyl, haloalkyl, alkenyl, alkynyl, aralkyl, cycloalkyl, aryl, heteroaralkyl, heteroaryl, (cycloalkyl)alkyl, cycloalkyl, (heterocycloalkyl)alkyl, or heterocycloalkyl;
$R^a$ and $R^b$ are each independently hydrogen or substituted or unsubstituted alkyl, alkenyl, alkynyl, aralkyl, cycloalkyl, aryl, heteroaralkyl, heteroaryl, (cycloalkyl)alkyl, cycloalkyl, (heterocycloalkyl)alkyl, or heterocycloalkyl; or
$R^a$ and $R^b$, together with the nitrogen atom to which they are attached, form a substituted or unsubstituted 5- or 6-membered heterocycloalkyl;
$R^c$ is H or substituted or unsubstituted alkyl, alkenyl, haloalkyl (cycloalkyl)alkyl, or cycloalkyl;

Pharmaceutical Agents and Compositions

Also provided herein are methods of synthesizing a pharmaceutical agent and/or composition, comprising preparing a compound of formula (I) or (Ia) according to a method as described herein and synthesizing the pharmaceutical agent and/or composition from the compound of formula (I) or (Ia), e.g., by carrying out one or more chemical reactions on the compound of formula (I) or (Ia) and/or combining the pharmaceutical agent with one or more pharmaceutically acceptable carriers and/or excipients.

The pharmaceutical agent and/or composition prepared from the compound of formula (I) or (Ia) may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Synthetic Schemes of Exemplary Pharmaceutical Products

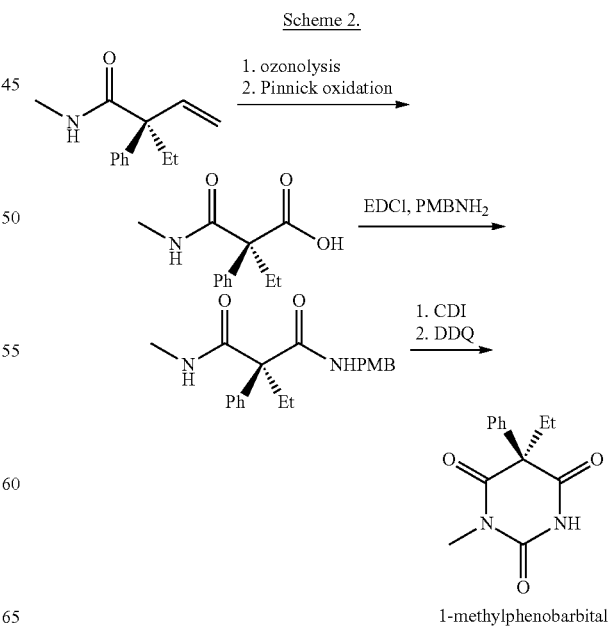

Scheme 3.
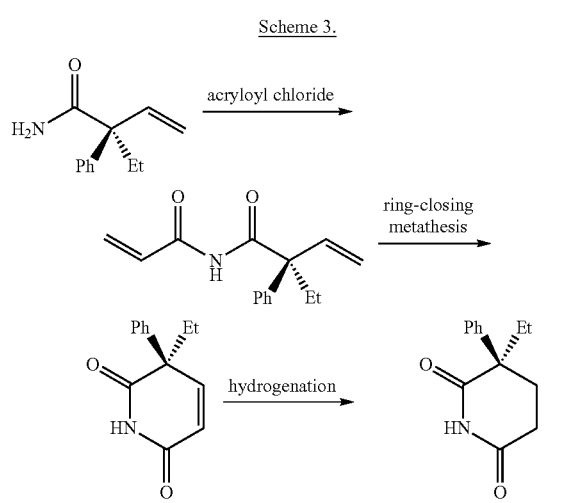
2-ethyl-2-phenylglutarimide
Scheme 4.
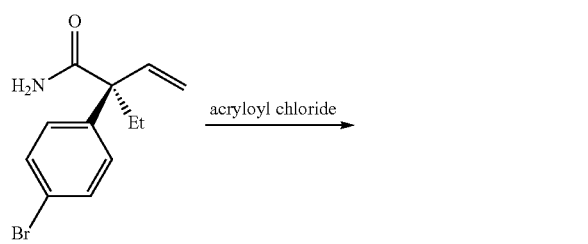
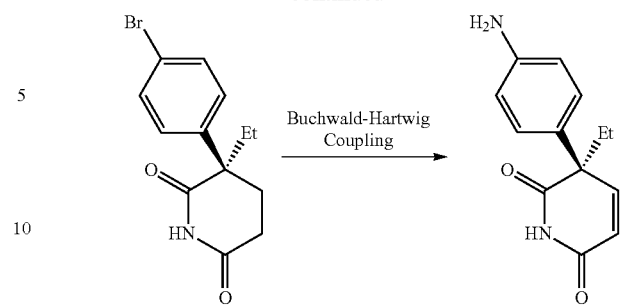
Scheme 5.
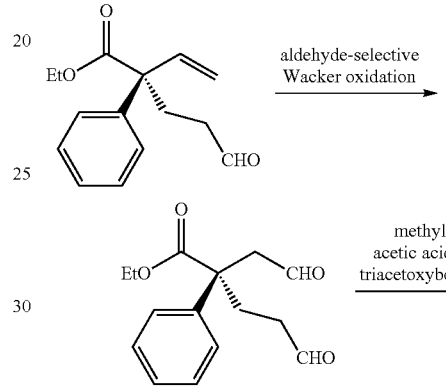
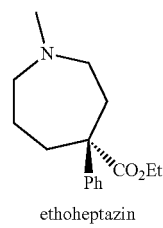
ethoheptazin
Scheme 6.
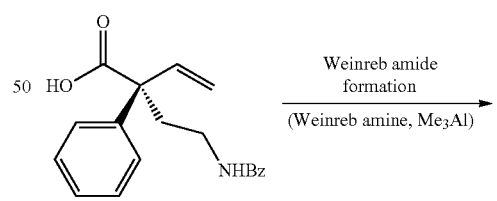
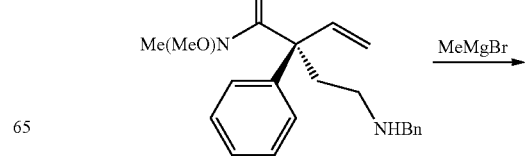

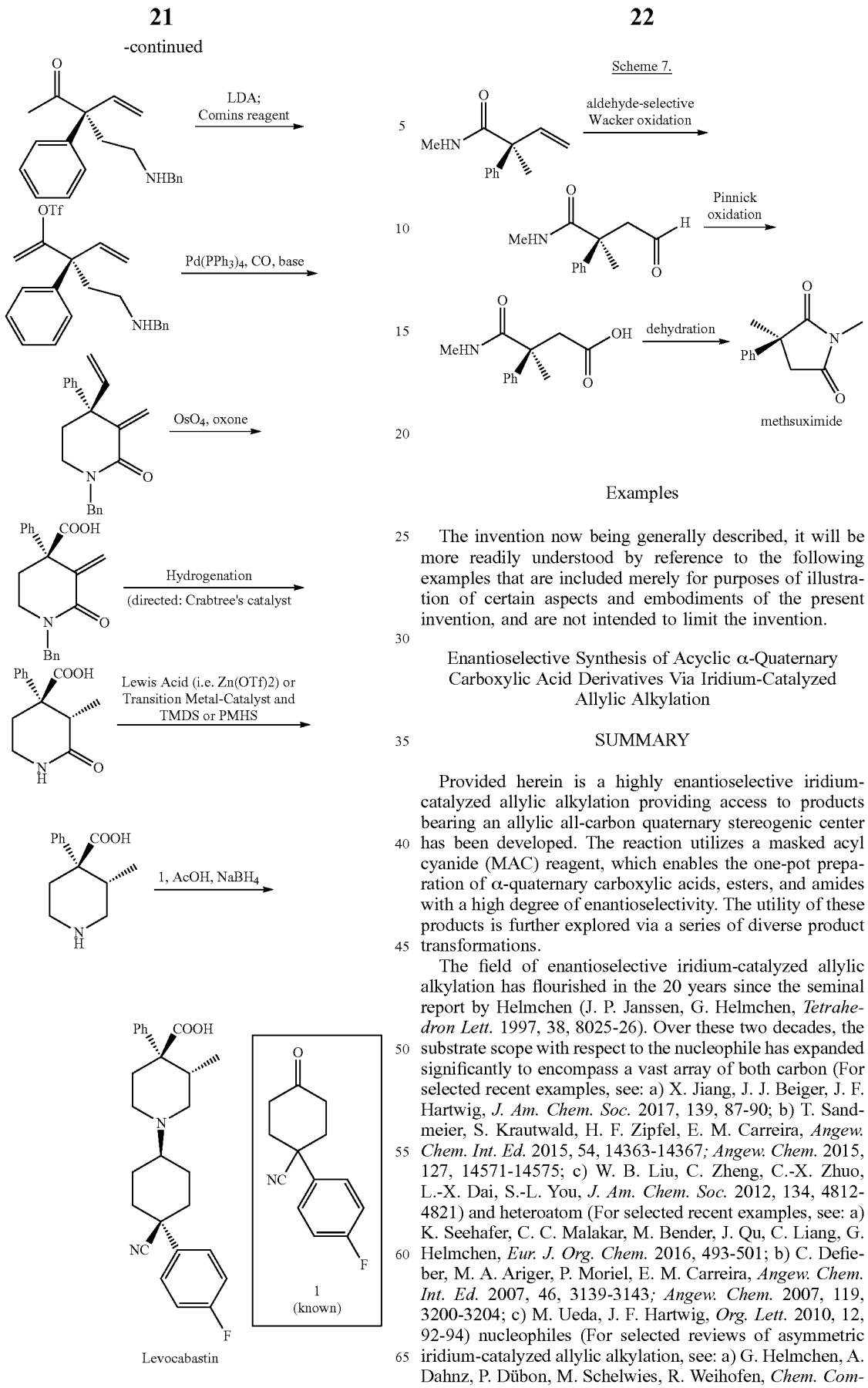

Examples

The invention now being generally described, it will be more readily understood by reference to the following examples that are included merely for purposes of illustration of certain aspects and embodiments of the present invention, and are not intended to limit the invention.

Enantioselective Synthesis of Acyclic α-Quaternary Carboxylic Acid Derivatives Via Iridium-Catalyzed Allylic Alkylation

SUMMARY

Provided herein is a highly enantioselective iridium-catalyzed allylic alkylation providing access to products bearing an allylic all-carbon quaternary stereogenic center has been developed. The reaction utilizes a masked acyl cyanide (MAC) reagent, which enables the one-pot preparation of α-quaternary carboxylic acids, esters, and amides with a high degree of enantioselectivity. The utility of these products is further explored via a series of diverse product transformations.

The field of enantioselective iridium-catalyzed allylic alkylation has flourished in the 20 years since the seminal report by Helmchen (J. P. Janssen, G. Helmchen, *Tetrahedron Lett.* 1997, 38, 8025-26). Over these two decades, the substrate scope with respect to the nucleophile has expanded significantly to encompass a vast array of both carbon (For selected recent examples, see: a) X. Jiang, J. J. Beiger, J. F. Hartwig, *J. Am. Chem. Soc.* 2017, 139, 87-90; b) T. Sandmeier, S. Krautwald, H. F. Zipfel, E. M. Carreira, *Angew. Chem. Int. Ed.* 2015, 54, 14363-14367; *Angew. Chem.* 2015, 127, 14571-14575; c) W. B. Liu, C. Zheng, C.-X. Zhuo, L.-X. Dai, S.-L. You, *J. Am. Chem. Soc.* 2012, 134, 4812-4821) and heteroatom (For selected recent examples, see: a) K. Seehafer, C. C. Malakar, M. Bender, J. Qu, C. Liang, G. Helmchen, *Eur. J. Org. Chem.* 2016, 493-501; b) C. Defieber, M. A. Ariger, P. Moriel, E. M. Carreira, *Angew. Chem. Int. Ed.* 2007, 46, 3139-3143; *Angew. Chem.* 2007, 119, 3200-3204; c) M. Ueda, J. F. Hartwig, *Org. Lett.* 2010, 12, 92-94) nucleophiles (For selected reviews of asymmetric iridium-catalyzed allylic alkylation, see: a) G. Helmchen, A. Dahnz, P. Dübon, M. Schelwies, R. Weihofen, *Chem. Commun.* 2007, 675-691; b) J. F. Hartwig, M. J. Pouy, *Top.*

*Organomet. Chem.* 2011, 34, 169-208; c) W.-B. Liu, J.-B. Xia, S.-L. You, Top. *Organomet. Chem.* 2012, 38, 155-208; d) J. C. Hethcox, S. E. Shockley, B. M. Stoltz, *ACS Catal.* 2016, 6, 6207-6213). Conversely, the scope of the electrophiles has remained largely unchanged, being limited to those that produce products bearing a tertiary allylic stereocenter (Scheme 1a, left) (A singular example of an iridium-catalyzed allylic alkylation reaction producing a product bearing an allylic all-carbon stereocenter has been reported with 11% yield and 21% ee: G. Onodera, K. Watabe, M. Matsubara, K. Oda, S. Kezuka, R. Takeuchi, *Adv. Synth. Catal.* 2008, 350, 2725-2732). Despite the longstanding interest in the synthesis of enantioenriched quaternary stereocenters within the synthetic community as well as the development of other transition metal-catalyzed processes to access all-carbon quaternary allylic stereocenters (a) C. J. Douglas, L. E. Overman, *Proc. Natl. Acad. Sci. USA* 2004, 101, 5363-5367; b) J. P. Das, I. Marek, *Chem. Commun.* 2011, 47, 4593-4623; c) K. W. Quasdorf. L. E. Overman, *Nature* 2014, 516, 181-191; d) E. J. Corey, A. Guzman-Perez, *Angew. Chem. Int. Ed.* 1998, 37, 388-401; *Angew. Chem.* 1998, 110, 402-415; e) J. Christoffers, A. Mann, *Angew. Chem. Int. Ed.* 2001, 40, 4591-4597; *Angew. Chem.* 2001, 113, 4725-4732; f) B. M. Trost, C. Jiang, *Synthesis* 2006, 369-396; g) Y. Liu, S.-J. Han, W.-B. Liu, B. M. Stoltz, *Acc. Chem. Res.* 2015, 48, 740-751; For selected recent examples of the enantioselective transition metal-catalyzed synthesis of allylic all-carbon quaternary stereocenters, see: a) A. Zhang, T. V. RajanBabu, *J. Am. Chem. Soc.* 2006, 128, 5620-5621; b) C. A. Falciola, A. Alexakis, *Chem. Eur. J.* 2008, 14, 10615-10627; c) Y. Xiong, G. Zhang, *Org. Lett.* 2016, 18, 5094-5097; d) S. Guduguntla, J.-B. Gualtierotti, S. S. Goh, B. L. Feringa, *ACS Catal.* 2016, 6, 6591-6595; e) B. M. Trost, C. Jiang, *J. Am. Chem. Soc.* 2001, 123, 12907-12908; f) X.-L. Hou, N. Sun, *Org. Lett.* 2004, 6, 4399-4401; g) P. Zhang, H. Le, R. E. Kyne, J. P. Morken, *J. Am. Chem. Soc.* 2011, 133, 9716-9719; For the only enantioselective reports to access acyclic quaternary α-vinyl, α-aryl carbonyl derivatives, see: a) K. E. Murphy, A. H. Hoveyda, *Org. Lett.* 2005, 7, 1255-1258; b) Y. Lee, A. H. Hoveyda, *J. Am. Chem. Soc.* 2006, 128, 15604-15605; c) F. Gao, Y. Lee, K. Mandai, A. H. Hoveyda, *Angew. Chem. Int. Ed.* 2010, 49, 8370-8374; *Angew. Chem.* 2010, 122, 8548-8552; d) K. Hojoh, H. Ohmiya, M. Sawamura, *J. Am. Chem. Soc.* 2017, 139, 2184-2187) iridium-catalyzed allylic alkylation reactions that furnish products possessing such a stereocenter remain conspicuously absent from the literature (Scheme 1a, right).

It was hypothesized that an umpolung strategy iridium-catalyzed allylic alkylation reaction of a trisubstituted allylic electrophile with a masked acyl cyanide (MAC) nucleophile would not only give rise to products containing an enantioenriched allylic all-carbon quaternary stereocenter, but also provide access to highly valuable acyclic α-quaternary carboxylic acid derivatives (i.e., acids, esters, amides) upon unmasking of the MAC functionality (Scheme 1b) (For the only enantioselective reports to access acyclic quaternary α-vinyl, α-aryl carbonyl derivatives, see: a) K. E. Murphy, A. H. Hoveyda, *Org. Lett.* 2005, 7, 1255-1258; b) Y. Lee, A. H. Hoveyda, *J. Am. Chem. Soc.* 2006, 128, 15604-15605; c) F. Gao, Y. Lee, K. Mandai, A. H. Hoveyda, *Angew. Chem. Int. Ed.* 2010, 49, 8370-8374; *Angew. Chem.* 2010, 122, 8548-8552; d) K. Hojoh, H. Ohmiya, M. Sawamura, *J. Am. Chem. Soc.* 2017, 139, 2184-2187; J. C. Hethcox, S. E. Shockley, B. M. Stoltz, *Org. Lett.* 2017, 19, 1527-1529; K. S. Yang, A. E. Nibbs, Y. E. Türkmen, V. H. Rawal, *J. Am. Chem. Soc.* 2013, 135, 16050-16053). However, success of this strategy hinged upon the implementation of a trisubstituted allylic electrophile, which was predicted to be unreactive in an enantioselective iridium-catalyzed allylic alkylation reaction. It is known that the reaction rates of these processes decrease with increasing substitution on the olefin of the electrophile (A singular example of an iridium-catalyzed allylic alkylation reaction producing a product bearing an allylic all-carbon stereocenter has been reported with 11% yield and 21% ee: G. Onodera, K. Watabe, M. Matsubara, K. Oda, S. Kezuka, R. Takeuchi, *Adv. Synth. Catal.* 2008, 350, 2725-2732; a) S. T. Madrahimov, J. F. Hartwig, *J. Am. Chem. Soc.* 2012, 134, 8136-8147; b) S. T. Madrahimov, Q. Li, A. Sharma, J. F. Hartwig, *J. Am. Chem. Soc.* 2015, 137, 14968-14981; One report of a trisubstituted allylic electrophile in an enantioselective iridium-catalyzed allylic alkylation has been disclosed, but like all known examples, the products bear a tertiary allylic stereocenter: M. Chen, J. F. Hartwig, *Angew. Chem. Int. Ed.* 2016, 55, 11651-11655; *Angew. Chem.* 2016, 128, 11823-11827). Herein, this heretofore unreactive class of electrophiles was unlocked to achieve the first example of an enantioselective iridium-catalyzed allylic alkylation reaction forming a quaternary stereocenter at the allylic position.

Scheme 1. Synthesis of allylic all-carbon quaternary stereocenters via enantioselective iridium-catalyzed allylic alkylation.

a) Limitations in Enantioselective Iridium-Catalyzed Allylic Alkylation b) This Research

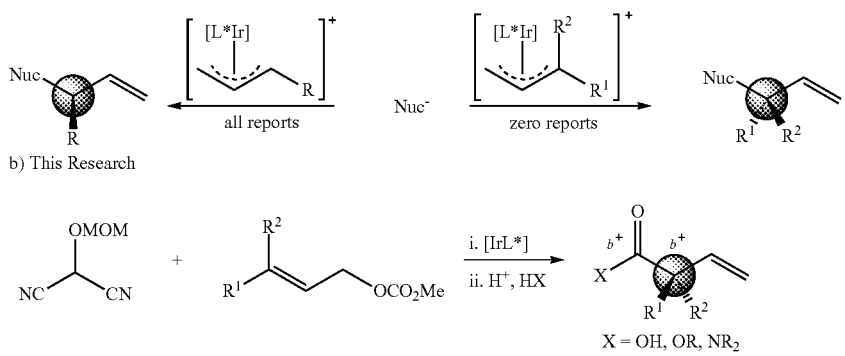

X = OH, OR, NR$_2$

Preliminary studies focused on identifying a combination of ligand and additive to promote the reaction of MAC 1 and trisubstituted allylic electrophile 2 (Table 1). Application of our standard conditions for iridium-catalyzed allylic alkylation reactions of [Ir(cod)Cl]$_2$, L1, and LiBr returned only starting material (Table 1, entry 1) (W.-B. Liu, C. M. Reeves, B. M. Stoltz, *J. Am. Chem. Soc.* 2013, 135, 17298-17301; J. C. Hethcox, S. E. Shockley, B. M. Stoltz, *Org. Lett.* 2017, 19, 1527-1529). A brief ligand screen revealed that while ligand L2 also resulted in no reaction (entry 2), the phosphoramidite L3 developed by Carreira provided desired product 3 in 13% yield with a moderate 79% ee (entry 3) (C. Defieber, M. A. Ariger, P. Moriel, E. M. Carreira, *Angew. Chem. Int. Ed.* 2007, 46, 3139-3143; *Angew. Chem.* 2007, 119, 3200-3204). Attempts to further increase yield and selectivity via an extensive evaluation of additives known to promote iridium-catalyzed allylic alkylations proved ineffective (For selected recent examples, see: a) X. Jiang, J. J. Beiger, J. F. Hartwig, *J. Am. Chem. Soc.* 2017, 139, 87-90; b) T. Sandmeier, S. Krautwald, H. F. Zipfel, E. M. Carreira, *Angew. Chem. Int. Ed.* 2015, 54, 14363-14367; *Angew. Chem.* 2015, 127, 14571-14575; c) W. B. Liu, C. Zheng, C.-X. Zhuo, L.-X. Dai, S.-L. You, *J. Am. Chem. Soc.* 2012, 134, 4812-4821; For selected recent examples, see: a) K. Seehafer, C. C. Malakar, M. Bender, J. Qu, C. Liang, G. Helmchen, *Eur. J. Org. Chem.* 2016, 493-501; b) C. Defieber, M. A. Ariger, P. Moriel, E. M. Carreira, *Angew. Chem. Int. Ed.* 2007, 46, 3139-3143; *Angew. Chem.* 2007, 119, 3200-3204; c) M. Ueda, J. F. Hartwig, *Org. Lett.* 2010, 12, 92-94; For selected reviews of asymmetric iridium-catalyzed allylic alkylation, see: a) G. Helmchen, A. Dahnz, P. Dübon, M. Schelwies, R. Weihofen, *Chem. Commun.* 2007, 675-691; b) J. F. Hartwig, M. J. Pouy, Top. *Organomet. Chem.* 2011, 34, 169-208; c) W.-B. Liu, J.-B. Xia, S.-L. You, Top. *Organomet. Chem.* 2012, 38, 155-208; d) J. C. Hethcox, S. E. Shockley, B. M. Stoltz, *ACS Catal.* 2016, 6, 6207-6213; (a) S. T. Madrahimov, J. F. Hartwig, *J. Am. Chem. Soc.* 2012, 134, 8136-8147; b) S. T. Madrahimov, Q. Li, A. Sharma, J. F. Hartwig, *J. Am. Chem. Soc.* 2015, 137, 14968-14981).

It was hypothesized that the oxidative addition process is slow for trisubstituted allylic electrophiles, and it was reasoned that the inclusion of a strong Lewis acid would facilitate the ionization of the carbonate during the insertion event, leading to improved reactivity of these recalcitrant electrophiles. Toward this end, LiBr was substituted for triethylborane and it was found that the yield nearly tripled and the enantioselectivity rose to 93% ee (entry 4) (Only one report of a borane additive (Ph$_3$B) in iridium-catalyzed allylic alkylation reactions has been disclosed: Y. Yamashita, A. Gopalarathnam, J. F. Hartwig *J. Am. Chem. Soc.* 2007, 129, 7508-7509). Upon varying the stoichiometry of nucleophile 1 to electrophile 2, a dramatic increase in yield to 74% was observed with no erosion of enantioselectivity (entry 5). Ultimately, it was found that exposure of a mixture (1:2) of MAC 1 and trisubstituted allylic electrophile 2 to a catalyst prepared from [Ir(cod)Cl]$_2$ (2 mol %), L3 (4.2 mol %), and TBD (10 mol %) in the presence of triethylborane (200 mol %) at 60° C. afforded MAC adduct 3 in nearly quantitative yield and in 94% ee (entry 6) (It should be noted that excess electrophile 2 is not consumed via a side reaction and therefore can be recovered following the iridium-catalyzed allylic alkylation reaction).

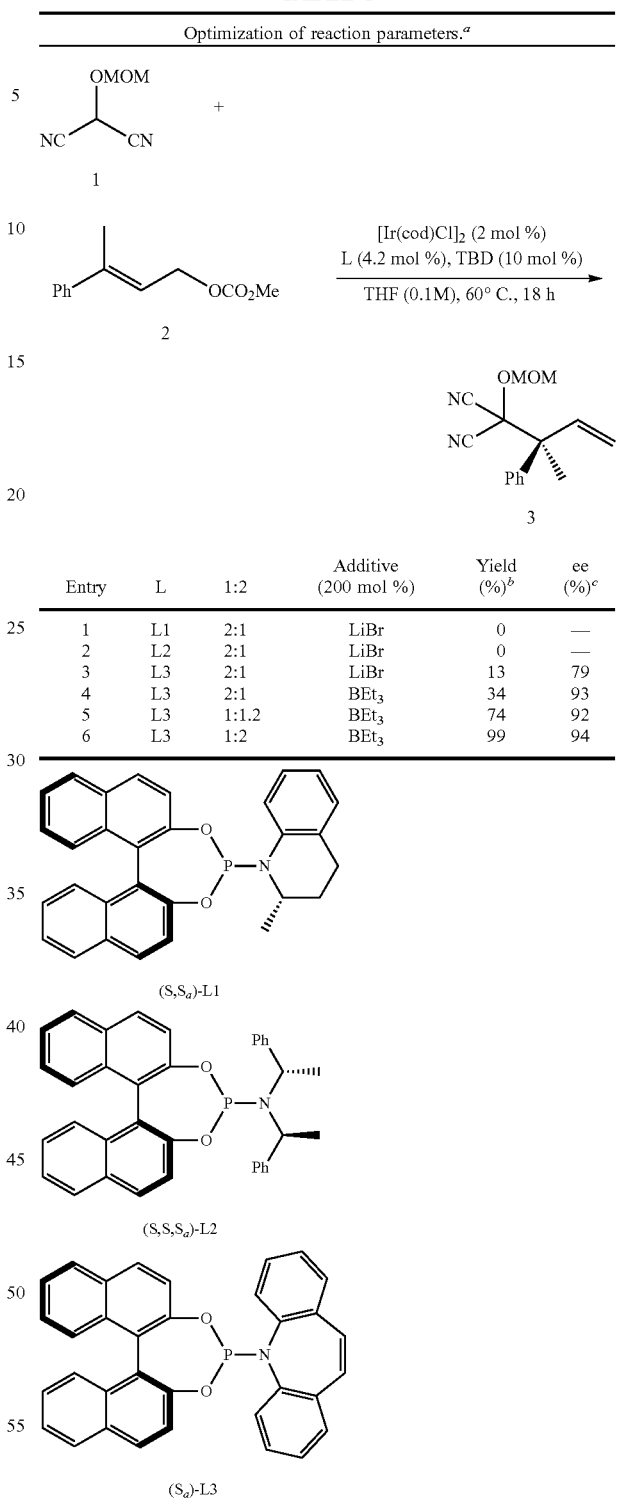

TABLE 1

Optimization of reaction parameters.[a]

| Entry | L | 1:2 | Additive (200 mol %) | Yield (%)[b] | ee (%)[c] |
|---|---|---|---|---|---|
| 1 | L1 | 2:1 | LiBr | 0 | — |
| 2 | L2 | 2:1 | LiBr | 0 | — |
| 3 | L3 | 2:1 | LiBr | 13 | 79 |
| 4 | L3 | 2:1 | BEt$_3$ | 34 | 93 |
| 5 | L3 | 1:1.2 | BEt$_3$ | 74 | 92 |
| 6 | L3 | 1:2 | BEt$_3$ | 99 | 94 |

[a]Reactions performed on 0.1 mmol scale.
[b]$^1$H NMR yield based on internal standard.
[c]Determined by chiral HPLC analysis.
[d]TBD = 1,3,5-triazabicyclo[4.4.0]dec-5-ene.

The guanidine base TBD was found necessary for the reaction. The importance of electrophile stereochemistry was also observed. Though previously reported conditions for the use of L3 in iridium-catalyzed allylic alkylations do not require a base additive (S. L. Rössler, S. Krautwald, E.

M. Carreira, *J. Am. Chem. Soc.* 2017, 139, 3603-3606), it was found the inclusion of TBD during the catalyst prestir to be critical to the success of the reaction. It was hypothesized that TBD may be serving as either a placeholder ligand to prevent the formation of an inactive catalyst (TBD is included with ligands L1 and L2 to form an active iridicycle catalyst; however, Carreira has demonstrated that ligand L3 does not form an iridicycle) or as a base to promote the formation of an active iridicycle (X. Jiang, J. J. Beiger, J. F. Hartwig, *J. Am. Chem. Soc.* 2017, 139, 87-90; W. B. Liu, C. Zheng, C.-X. Zhuo, L.-X. Dai, S.-L. You, *J. Am. Chem. Soc.* 2012, 134, 4812-4821). Additionally, it was noted that use of the E-trisubstituted allylic electrophile was required, as Z-olefin isomer 4 led to markedly decreased yield and selectivity (Table 2). Moreover, neither a kinetic nor a dynamic kinetic resolution occurred under the reaction conditions with the use of terminal olefin rac-5 (Table 2). The difference in reactivity was rationalized via the preferred conformation of the reactants. Whereas 2 may exist in a planar conformation, the phenyl group of 4 likely prefers to rotate out of plane to alleviate $A^{1,3}$ strain. In adopting this perpendicular conformation, the phenyl ring has now increased the sterics above and below the olefin as well as become σ-withdrawing rather than π-donating. The combination of increased sterics and decreased electron density is believed to contribute to the lower reactivity.

TABLE 2

Electrophile Isomers.[a]

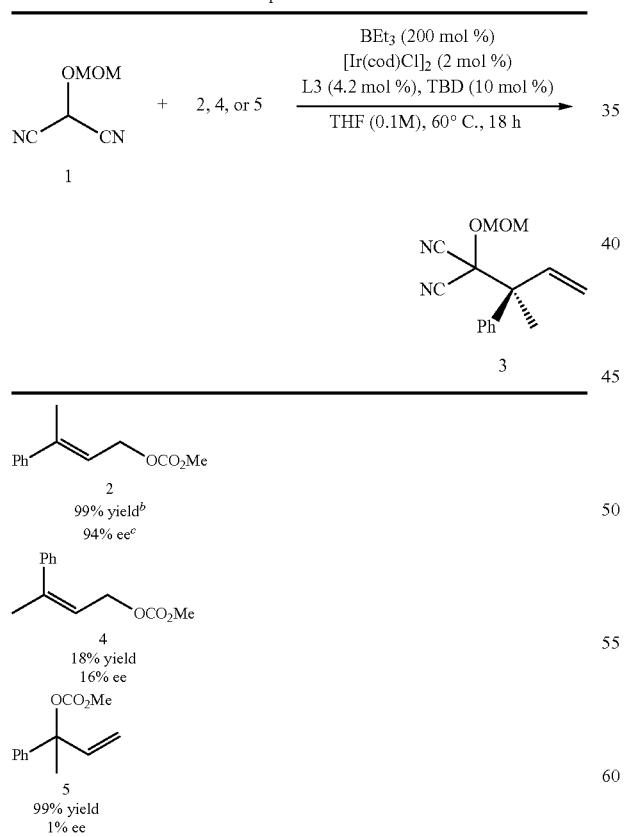

[a]Reactions performed with 1 (0.1 mmol) and 2, 4, or 5 (0.2 mmol).
[b]$^1$H NMR yield based on internal standard.
[c]Determined by chiral HPLC analysis.

Before substrate scope exploration commenced, it was identified an additional opportunity for innovation. It was envisoned that hydrolysis of the MAC functionality of product 3 could be performed in the same reaction vessel as the iridium-catalyzed allylic alkylation reaction to provide direct access to the corresponding carboxylic acid in a one-pot, two-step procedure (K. S. Yang, A. E. Nibbs, Y. E. Türkmen, V. H. Rawal, *J. Am. Chem. Soc.* 2013, 135, 16050-16053). Moreover, it was envisioned that these carboxylic acid products would be amenable to purification by a simple acid/base extraction. To this end, the crude allylic alkylation mixture was subjected to to hydrolysis with 6M HCl at 80° C., and it was found that pure carboxylic acid 7a was obtained after an aqueous work-up with no need for column chromatography (Table 3).

TABLE 3

Aryl Substituent Substrate Scope.[a]

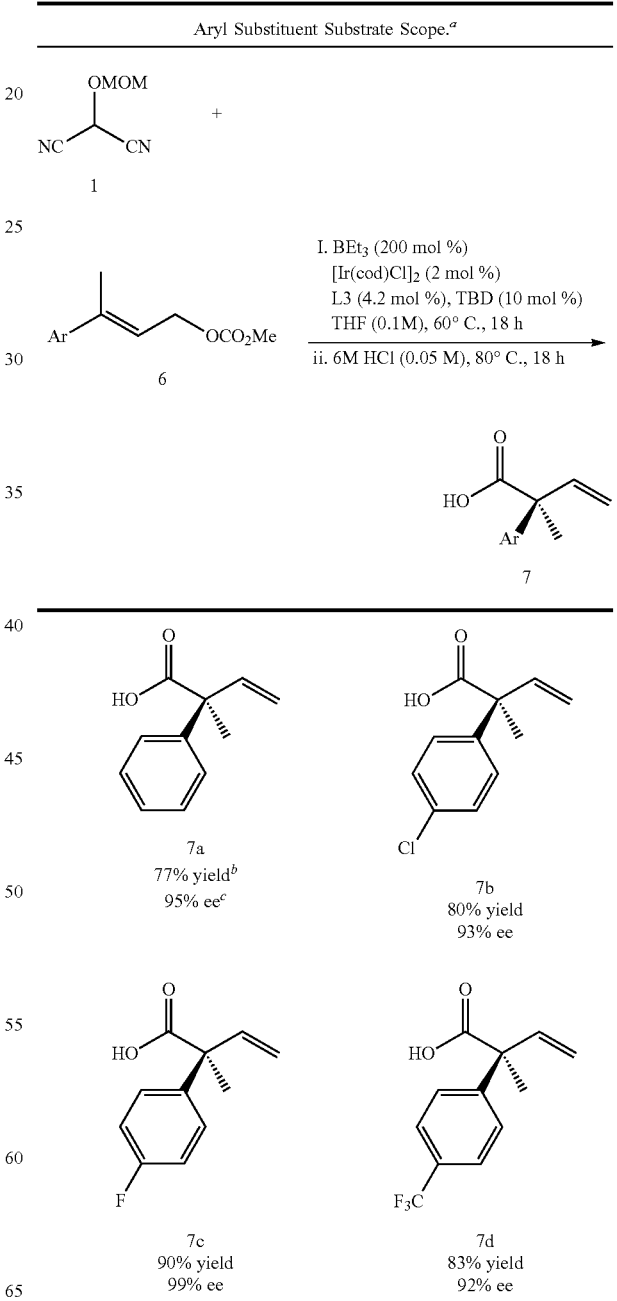

TABLE 3-continued

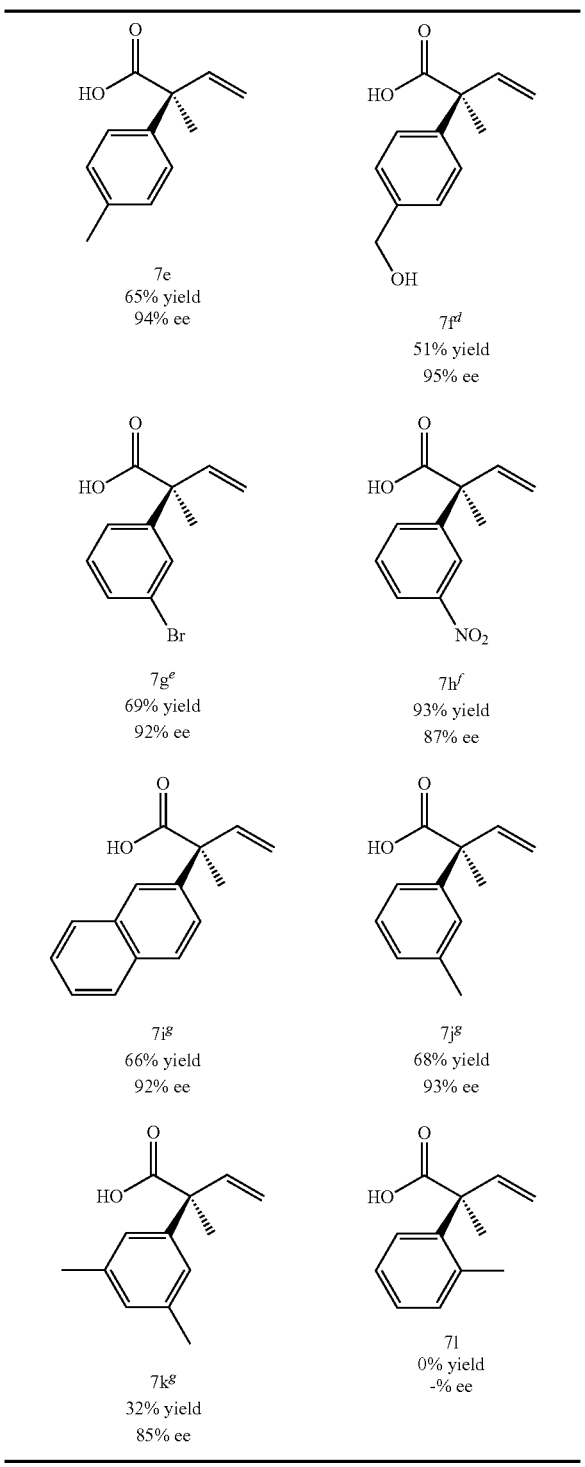

[a] Reactions performed on 0.2 mmol scale.
[b] Isolated yield.
[c] Determined by chiral HPLC or SFC analysis.
[d] Electrophile 6f used as the bis-carbonate which was deprotected during hydrolysis.
[e] Reaction run for 48 h.
[f] Absolute stereochemistry determined via single crystal X-ray analysis.
[g] Reaction performed with double catalyst loading.

With the optimized protocol in hand, the effect of substitution on the aryl moiety of electrophile 6 (Table 3) was explored. It was found that para-substitution was well tolerated for a range of substituents (—Cl, —F, —CF$_3$, -Me, and —CH$_2$OH) to provide acids 7b-f in consistently high enantioselectivities, though electron-rich substrates provided decreased yields. Meta-substituted products 7g and 7h were obtained in similarly high enantioselectivites (92% and 87% ee, respectively), and bulky naphthyl-substituted acid 7i was furnished in 92% ee, albeit in a moderate 66% yield. Further exploration of steric effects using methyl-substituted derivatives demonstrated that while a single meta-substituent is tolerated to access 7j in 68% yield with 93% ee, the bis-meta-substituted derivative 7k was afforded in a drastically lower 32% yield but with good enantioselectivity (85% ee). Finally, it was found that ortho-substitution was not tolerated and only starting material was recovered from the reaction. Thiophene- and furan-substituted allylic electrophiles were well tolerated in the iridium-catalyzed allylic alkylation reaction but were not amenable to the hydrolysis conditions.

TABLE 4

Non-Aryl Substituent Substrate Scope.[a]

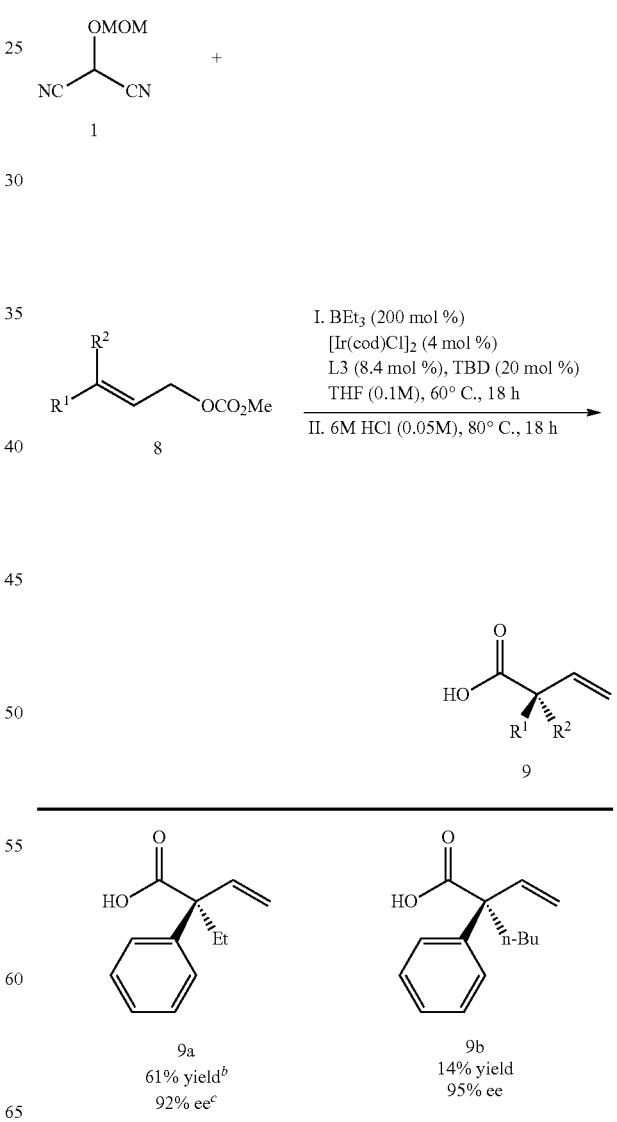

TABLE 4-continued

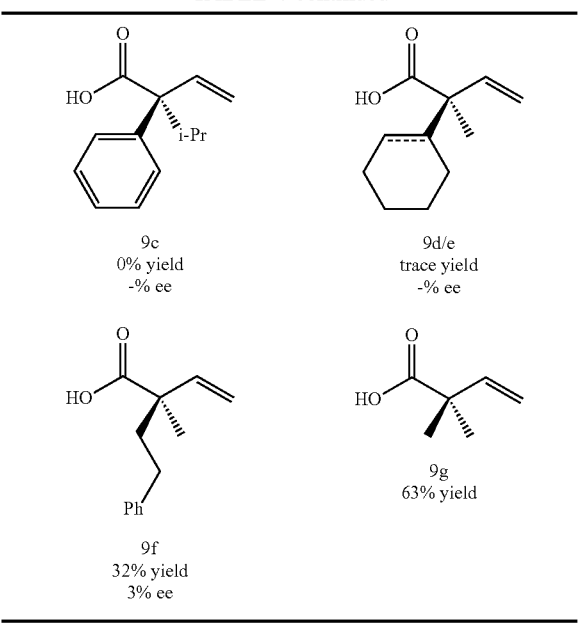

9c
0% yield
-% ee

9d/e
trace yield
-% ee 9f
32% yield
3% ee 9g
63% yield

[a] Reactions performed on 0.2 mmol scale.
[b] Isolated yield.
[c] Determined by chiral HPLC or SFC analysis.

With the general trends in reactivity corresponding to aryl substitution elucidated, the scope of the reaction with respect to the aliphatic moiety of the electrophile (Table 4) was next explored. It was found that extension of the alkyl chain led to decreased yields with ethyl-substituted 9a and n-butyl-substituted 9b isolated in 61% and 14% yield, respectively, though both were obtained in similarly excellent enantioselectivities. Furthermore, branched-substituted electrophiles were unreactive and only starting material was recovered in attempts to prepare isopropyl-substituted 9c.

The necessity of the aryl functionality was next explored. It was hypothesized that cyclohexyl- and cyclohexenyl-substituted electrophiles 8d and 8e would mimic the sterics of the phenyl moiety of 6a when interacting with the chiral catalyst, but it was found that only trace products 9d and 9e were observed under our reaction conditions (Table 4). Use of bis-n-alkyl-substituted electrophile 8f provided the corresponding acid 9f in moderate yield, though no enantioselectivity was observed. Finally, it was found that prenyl methyl carbonate (8g) was a competent electrophile furnishing acid 9g in 63% yield.

As MAC adducts can be transformed to essentially any carboxylic acid derivative, additional one-pot transformations to access both α-quaternary esters and amides were also developed. It was found that alkanolysis of the crude MAC alkylation product with either methanol or allyl alcohol provided methyl ester 10 and allyl ester 11 in 88% and 74% yield, respectively (Scheme 2). Similarly, aminolysis provided access to both tertiary amide 12 in 61% yield and secondary amide 13 in 63% yield.

Scheme 2.

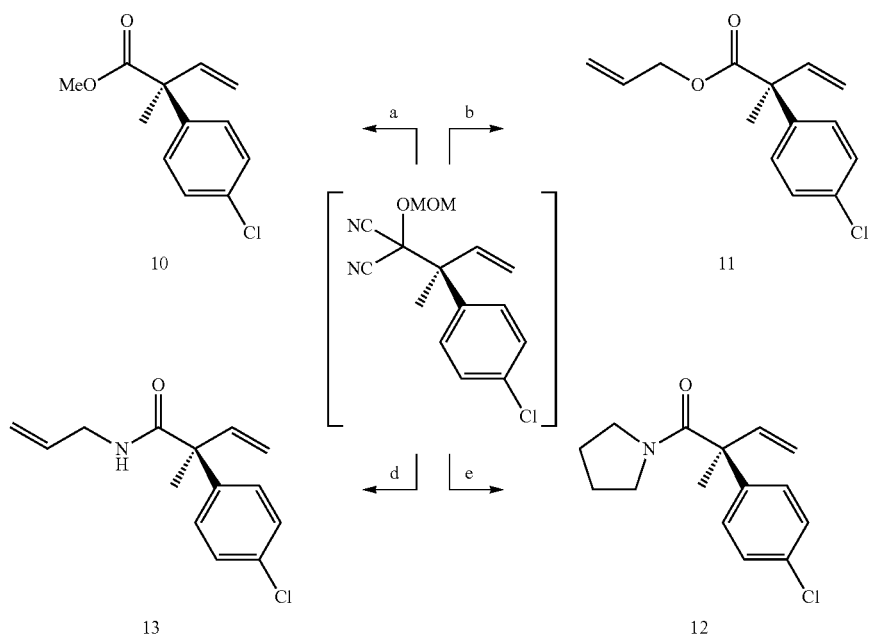

a i. CSA, AcOH/DME, 60° C., 6 h, ii. MeOH, Et$_3$N, -40° C.→23° C., 18 h, 88% yield;
b i. CSA, AcOH/DME, 60° C., 6 h, ii. allyl alcohol, Et$_3$N, 0° C.→23° C., 18 h, 74% yield;
c CSA, AcOH/DME, 60° C., 6 h, ii. pyrrolidine, Et$_3$N, -40° C.→23° C., 18 h, 61% yield;
d i. CSA, AcOH/DME, 60° C., 6 h, ii. allyl amine, Et$_3$N, 0° C.→23° C., 18 h, 63% yield.

In order to demonstrate the synthetic utility of the enantioenriched α-quaternary carboxylic acid derivatives, a series of transformations were performed to access a diverse array of chiral building blocks starting from ester derivative 10 (Scheme 3). Hydrogenation of olefin 10 proceeded smoothly to deliver ethyl-substituted 14 in 97% yield. Alcohol 15 was accessed via reduction of the ester moiety in 73% yield (For direct access to these products see: K. D. Nguyen, D. Herkommer, M. J. Krische, *J. Am. Chem. Soc.* 2016, 138, 14210-14213). Dihydroxylation of the pendant olefin proceeded with concomitant lactonization to furnish γ-butyrolactone 16 in 82% yield as a mixture (1:1) of diastereomers. Finally, ozonolysis delivered aldehyde 17 in moderate yield.

Scheme 3.

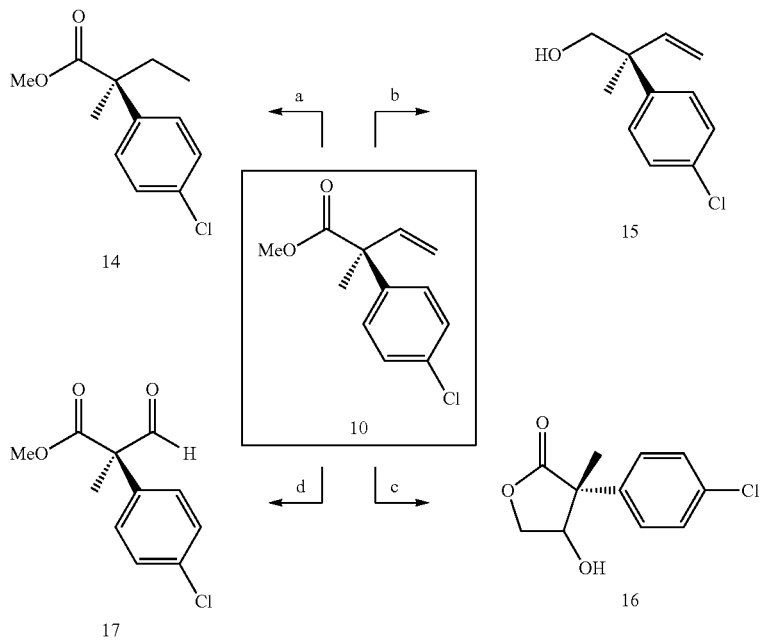

a Pd/C, H$_2$ (balloon), EtOAc, 23° C., 18 h, 97% yield;
b DIBAL, Et$_2$O, 0° C., 2 h, 73% yield;
c K$_2$OsO$_4$, NMO, THF/H$_2$O (4:1), 23° C., 18 h, 82% yield (1:1 dr);
d i. O$_3$, NaHCO$_3$, MeOH/CH$_2$Cl$_2$ (1:5), -78° C., 0.5 h, ii. DMS, -78° C.→23° C., 18 h, 50% yield.

In conclusion, developed herein is the first synthesis of all-carbon quaternary allylic stereocenters via enantioselective iridium-catalyzed allylic alkylation. The unprecedented combination of triethylborane and a catalyst prepared from [Ir(cod)Cl]$_2$, L3, and TBD was used to coerce reactivity from a once poorly reactive class of trisubstituted allylic electrophiles. Furthermore, the use of a single masked acyl cyanide nucleophile facilitated the one-pot syntheses of enantioenriched α-quaternary acids, esters, and amides. The protocol is tolerant of a wide range of substitution on the aryl moiety to provide the corresponding products with good yields and excellent enantioselectivites. This methodology is critical in laying the groundwork for the future development of technology to access vicinal quaternary stereocenters via iridium-catalyzed allylic alkylation of prochiral nucleophiles.

Materials and Methods

Unless otherwise stated, reactions were performed in flame-dried glassware under an argon or nitrogen atmosphere using dry, deoxygenated solvents. Solvents were dried by passage through an activated alumina column under argon. Commercially obtained reagents were used as received. Chemicals were purchased from Sigma Aldrich/Strem/Alfa Aesar/Oakwood Chemicals and used as received. Reaction temperatures were controlled by an IKAmag temperature modulator. Glove box manipulations were performed under a nitrogen atmosphere. Thin-layer chromatography (TLC) and preparatory TLC was performed using E. Merck silica gel 60 F254 precoated plates (0.25 mm) and visualized by UV fluorescence quenching, KMnO$_4$, or p-anisaldehyde staining. SiliaFlash P60 Academic Silica gel (particle size 0.040-0.063 mm) was used for flash chromatography. Analytical chiral HPLC was performed with an Agilent 1100 Series HPLC utilizing a Chiralpak IC column (4.6 mm×25 cm) or a Chiralpak AD-H column (4.6 mm×25 cm), both obtained from Daicel Chemical Industries, Ltd. with visualization at 210 nm. Analytical SFC was performed with a Mettler SFC supercritical CO$_2$ analytical chromatography system utilizing a Chiralpak AD-H column (4.6 mm×25 cm) obtained from Daicel Chemical Industries, Ltd. with visualization at 210 nm. Preparatory HPLC was performed with an Agilent 1200 Series HPLC equipped with a Viridis SFC 2-Ethylpyridine 5 µm column (4.6×250 mm). $^1$H NMR spectra were recorded on a Bruker Avance HD 400 MHz spectrometer and are reported relative to residual CHCl$_3$ (δ 7.26 ppm). $^{13}$C NMR spectra were recorded on a Bruker Avance HD 400 MHz spectrometer and are reported relative to residual CDCl$_3$ (δ 77.16 ppm). Data for $^1$H NMR are reported as follows: s=singlet, d=doublet, t=triplet, q=quartet, p=pentet, sept=septuplet, m=multiplet, br s=broad singlet. Data for $^{13}$C NMR are reported in terms of chemical shifts (δ ppm). Some reported spectra include minor solvent impurities of benzene (δ 7.36 ppm), water (δ 1.56 ppm), ethyl acetate (δ 4.12, 2.05, 1.26 ppm), methylene chloride (δ 5.30 ppm), grease (δ 1.26, 0.86 ppm), and/or silicon grease (δ 0.07 ppm), which do not impact product assignments. IR spectra were obtained using a Perkin Elmer Paragon 1000 spectrometer using thin films deposited on NaCl plates and reported in frequency of absorption (cm$^{-1}$). High resolution mass spectra (HRMS) were obtained from the Caltech Mass Spectral Facility using a JEOL JMS-600H High Resolution Mass Spectrometer in fast atom bombardment (FAB+) or electron ionization (EI+) mode, or an Agilent 6200 Series TOF with an Agilent G1978A Multimode source in electrospray ionization (ESI+), atmospheric pressure chemical ionization (APCI+), or mixed ionization mode (MM: ESI-APCI+). Optical rotations were measured with a Jasco P-2000 polarimeter operating on the sodium D-line (589 nm), using a 100 mm pathlength cell and are reported as: $[\alpha]_D^T$ (concentration in g/100 mL, solvent).

List of Abbreviations ee—enantiomeric excess, HPLC—high-performance liquid chromatography, TLC—thin-layer chromatography, EtOAc—ethyl acetate, THF—tetrahydrofuran, MeOH—methanol, $Et_2O$—diethyl ether, IPA—isopropanol, AcOH—acetic acid, DME—dimethoxyethane, TBD—1,5,7-triazabicyclo[4.4.0]dec-5-ene, cod—cis,cis-1,5-cyclooctadiene, DIBAL—diisobutylaluminium hydride, dppp—1,3-bis(diphenylphosphino)propane, MAC—masked acyl cyanide, CSA—camphorsulfonic acid Preparation of Known Compounds Previously reported methods were used to prepare ligands $(S,S_a)$-L1 ((a) Liu, W.-B.; He, H.; Dai, L.-X.; You, S.-L. Synthesis 2009, 2076-82; (b) Liu, W.-B.; Zheng, C.; Zhuo, C.-X.; Dai, L.-X.; You, S.-L. J. Am. Chem. Soc. 2012, 134, 4812-21) and $(S_a)$-L3 (Hamilton, J. Y.; Sarlah, D.; Carreira, E. M. Org. Synth. 2015, 92, 1-12) as well as starting materials 1 ((a) Nemoto, H.; Li, X.; Ma, R.; Suzuki, I.; Shibuya, M. Tetrahedron Lett. 2003, 44, 73-75; (b) Yang, K. S.; Nibbs, A. E.; Türkmen, Y. E.; Rawal, V. H. J. Am. Chem. Soc. 2013, 135, 16050-53), 2 (Nakatsuji, H.; Ueno, K.; Misaki, T.; Tanabe, Y. Org. Lett. 2008, 10, 2131-34), 5 ((a) Ardolino, M. J.; Morken, J. P. J. Am. Chem. Soc. 2014, 136, 7092-100; (b) Evans, P. A.; Oliver, S.; Chae, J. J. Am. Chem. Soc. 2012, 134, 19314-17), 6a (Matsubara, R.; Jamison, T. F. J. Am. Chem. Soc. 2010, 132, 6880-81), 6b (Guzman-Martinez, A.; Hoveyda, A. H. J. Am. Chem. Soc. 2010, 132, 10634-37), 6d, 6e, 6j, 6l, 8a, 8d, and 8f) Gürtler, C.; Buchwald, S. L. Chem. Eur. J. 1999, 5, 3107-12).

Representative Procedures for the Synthesis of Electrophiles
Representative Procedure #1: Oxidative Heck Reaction (Ruan, J.; Li, X.; Saidi, O.; Xiao, J. J. Am. Chem. Soc. 2008, 130, 2424-25)

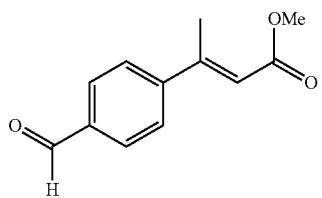

Methyl (E)-3-(4-formylphenyl)but-2-enoate (SI-1)

To a solution of (4-formylphenyl)boronic acid (0.75 g, 5.0 mmol, 1 equiv), $Pd(OAc)_2$ (23 mg, 0.10 mmol, 0.02 equiv), dppp (62 mg, 0.15 mmol, 0.03 equiv) in acetone (8 mL) was added methyl crotonate (1.1 mL, 10.0 mmol, 2 equiv) followed by trifluoroacetic acid (0.12 mL, 1.5 mmol, 0.3 equiv). The resulting slurry was heated under reflux for 48 h, whereupon the reaction was cooled to ambient temperature and concentrated under reduced pressure. The crude product was purified by silica gel flash column chromatography (5% EtOAc/hexanes) to give carbonate SI-1 as a colorless oil (0.17 g, 17% yield): $^1$H NMR (400 MHz, $CDCl_3$) δ 10.06 (s, 1H), 7.97-7.78 (m, 2H), 7.74-7.58 (m, 2H), 6.22 (q, J=1.3 Hz, 1H), 3.80 (s, 3H), 2.62 (d, J=1.4 Hz, 3H); $^{13}$C NMR (101 MHz, $CDCl_3$) δ 191.8, 167.0, 154.4, 148.2, 136.5, 130.1, 127.1, 119.0, 51.5, 18.1; IR (Neat Film, NaCl) 2950, 2839, 1704, 1631, 1605, 1434, 1349, 1273, 1214, 1171, 1036, 828 $cm^{-1}$; HRMS (FAB+) m/z calc'd for $C_{12}H_{13}O_3$ $[M+H]^+$: 205.0865, found 205.0860.

Representative Procedure #2: Reduction & Acylation

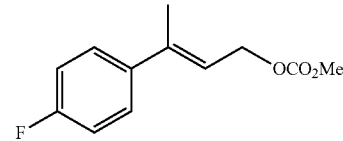

(E)-3-(4-Fluorophenyl)but-2-en-1-yl methyl carbonate (6c)

To a solution of methyl (E)-3-(4-fluorophenyl)but-2-enoate (Duan, Z.-C.; Hu, X.-P.; Zhang, C.; Zheng, Z. J. Org. Chem. 2010, 75, 8319-21) (0.30 g, 1.6 mmol, 1 equiv) in THF (3.1 mL) at −78° C. was added DIBAL (0.85 mL, 4.8 mmol, 3 equiv) dropwise. The resulting reaction mixture was stirred at −78° C. for 2.5 h, whereupon the reaction was quenched with a saturated aqueous Rochelle's salt solution (5 mL). The cooling bath was then removed and the reaction was stirred for 18 h at ambient temperature. The aqueous layer was extracted with $CH_2Cl_2$ (3×20 mL) and the combined organic layers were washed with brine (20 mL), dried over $Na_2SO_4$, and concentrated under reduced pressure.

The crude material was then dissolved in $CH_2Cl_2$ (6.4 mL) and cooled to 0° C. Pyridine (1.1 mL, 13 mmol, 8.3 equiv) was added followed by methyl chloroformate (0.28 mL, 3.7 mmol, 2.3 equiv) dropwise. The resulting solution was allowed to warm to ambient temperature and stirred for 18 h. The reaction was quenched with the addition of 1 M HCl (5 mL) and the aqueous layer was extracted with $CH_2Cl_2$ (3×20 mL). The combined organic layers were washed with brine (20 mL), dried over $Na_2SO_4$, and concentrated under reduced pressure. The crude product was purified by silica gel flash column chromatography (5% EtOAc/hexanes) to give carbonate 6c as a colorless solid (0.14 g, 38% yield): $^1$H NMR (400 MHz, $CDCl_3$) δ 7.40-7.33 (m, 2H), 7.05-6.96 (m, 2H), 5.87 (tq, J=7.0, 1.4 Hz, 1H), 4.84 (dd, J=7.1, 0.8 Hz, 2H), 3.80 (s, 3H), 2.11 (dd, J=1.4, 0.7 Hz, 3H).; $^{13}$C NMR (101 MHz, $CDCl_3$) δ 163.7, 161.3, 156.0, 140.2, 138.6 (d, J=3.3 Hz), 127.6 (d, J=8.0 Hz), 120.7 (d, J=1.3 Hz), 115.4, 115.1, 65.0, 55.0, 16.5; IR (Neat Film, NaCl) 2961, 1896, 1742, 1649, 1589, 1468, 1442, 1379, 1334, 1252, 1110, 994, 960, 945, 825, 794 $cm^{-1}$; HRMS (FAB+) m/z calc'd for $Cl_2H_{13}FO_3$ $[M]^+$: 224.0849, found 224.0850.

Spectroscopic Data for the Synthesis of Electrophiles

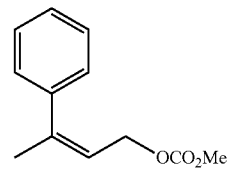

(Z)-methyl (3-phenylbut-2-en-1-yl) carbonate (4)

Carbonate 4 was prepared from ethyl (Z)-3-phenylbut-2-enoate (Nakatsuji, H.; Ueno, K.; Misaki, T.; Tanabe, Y. *Org. Lett.* 2008, 10, 2131-34) according to Representative Procedure #2 and isolated by silica gel flash column chromatography (5% EtOAc/hexanes) as a colorless oil (0.18 g, 49% yield): $^1$H NMR (400 MHz, CDCl$_3$) δ 7.41-7.18 (m, 5H), 5.76-5.68 (m, 1H), 4.58 (dd, J=7.2, 1.1 Hz, 2H), 3.79 (s, 3H), 2.13 (q, J=1.2 Hz, 3H); $^{13}$C NMR (101 MHz, CDCl$_3$) δ 155.8, 143.8, 140.3, 128.4, 127.8, 127.6, 120.5, 65.8, 54.8, 25.6; IR (Neat Film, NaCl) 3023, 2956, 1748, 1494, 1441, 1382, 1350, 1263, 1024, 944, 792, 765, 702 cm$^{-1}$; HRMS (FAB+) m/z calc'd for C$_{12}$H$_{15}$O$_3$ [M+H]$^+$: 207.1021, found 207.1011.

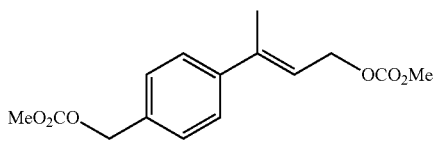

(E)-3-(4-(((Methoxycarbonyl)oxy)methyl)phenyl)but-2-en-1-yl methyl carbonate (6f)

Carbonate 6f was prepared from SI-1 according to Representative Procedure #2 and isolated by silica gel flash column chromatography (5% EtOAc/hexanes) as a colorless solid (0.11 g, 46% yield): $^1$H NMR (400 MHz, CDCl$_3$) δ 7.44-7.31 (m, 4H), 5.98-5.88 (m, 1H), 5.15 (s, 2H), 4.85 (dd, J=7.0, 0.9 Hz, 2H), 3.802 (s, 3H), 3.795 (s, 3H), 2.13-2.10 (m, 3H); $^{13}$C NMR (101 MHz, CDCl$_3$) δ 156.0, 155.9, 142.8, 140.6, 134.7, 128.5, 126.3, 121.2, 69.4, 65.0, 55.1, 55.0, 16.4; IR (Neat Film, NaCl) 2959, 1754, 1443, 1385, 1333, 1288, 958, 909, 794, 731 cm$^{-1}$; HRMS (FAB+) m/z calc'd for C$_{15}$H$_{18}$O$_6$ [M]$^+$: 294.1103, found 294.1098.

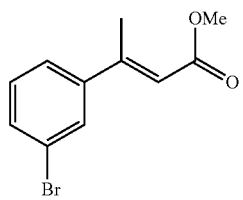

Methyl (E)-3-(3-bromophenyl)but-2-enoate (SI-2)

Ester SI-2 was prepared from (3-bromophenyl)boronic acid according to Representative Procedure #1 and isolated by silica gel flash column chromatography (3% EtOAc/hexanes) as a colorless oil (0.54 g, 42% yield): $^1$H NMR (400 MHz, CDCl$_3$) δ 7.65-7.59 (m, 1H), 7.51 (ddd, J=7.9, 2.0, 1.0 Hz, 1H), 7.45-7.37 (m, 1H), 7.31-7.26 (m, 1H), 6.14 (q, J=1.3 Hz, 1H), 3.78 (d, J=1.2 Hz, 3H), 2.57 (d, J=1.4 Hz, 3H); $^{13}$C NMR (101 MHz, CDCl$_3$) δ 167.1, 154.3, 144.4, 132.1, 130.2, 129.6, 125.1, 122.8, 117.9, 51.4, 18.1; IR (Neat Film, NaCl) 3062, 2948, 1719, 1631, 1558, 1435, 1346, 1274, 1191, 1168, 1037, 869, 785, 688 cm$^{-1}$; HRMS (FAB+) m/z calc'd for C$_{11}$H$_{12}$O$_2$Br [M+H]$^+$: 255.0021, found 255.0020.

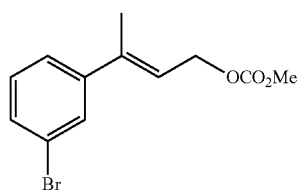

(E)-3-(3-Bromophenyl)but-2-en-1-yl methyl carbonate (6g)

Carbonate 6g was prepared from SI-2 according to Representative Procedure #2 and isolated by silica gel flash column chromatography (5% EtOAc/hexanes) as a colorless oil (0.47 g, 78% yield): $^1$H NMR (400 MHz, CDCl$_3$) δ 7.54 (t, J=1.8 Hz, 1H), 7.40 (ddd, J=7.9, 1.9, 1.0 Hz, 1H), 7.32 (ddd, J=7.8, 1.8, 1.0 Hz, 1H), 7.22-7.14 (m, 1H), 5.96-5.88 (m, 1H), 4.88-4.76 (m, 2H), 3.81 (s, 3H), 2.12-2.08 (m, 3H); $^{13}$C NMR (101 MHz, CDCl$_3$) δ 155.93, 144.65, 139.74, 130.68, 129.96, 129.18, 124.64, 122.65, 122.08, 64.84, 55.02, 16.38; IR (Neat Film, NaCl) 2955, 1748, 1590, 1558, 1442, 1376, 1332, 1263, 946, 789, 690 cm$^{-1}$; HRMS (FAB+) m/z calc'd for C$_{12}$H$_{13}$O$_3$Br [M]$^+$: 284.0048, found 284.0073.

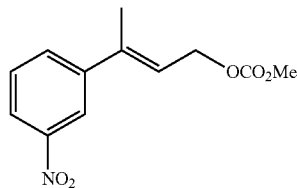

(E)-Methyl (3-(3-nitrophenyl)but-2-en-1-yl) carbonate (6h)

Carbonate 6h was prepared from methyl (E)-3-(3-nitrophenyl)but-2-enoate (Ho Oh, C.; Jung, H. H.; Kim, K. S.; Kim, N. *Angew. Chem. Int. Ed.* 2003, 42, 805-08) according to Representative Procedure #2 and isolated by silica gel flash column chromatography (10% EtOAc/hexanes) as a colorless oil (0.47 g, 78% yield): $^1$H NMR (400 MHz, CDCl$_3$) δ 8.26 (t, J=2.0 Hz, 1H), 8.14 (ddd, J=8.2, 2.3, 1.0 Hz, 1H), 7.73 (ddd, J=7.8, 1.8, 1.1 Hz, 1H), 7.51 (t, J=8.0 Hz, 1H), 6.10-5.91 (m, 1H), 4.88 (dt, J=6.9, 0.8 Hz, 2H), 3.82 (s, 3H), 2.18 (dd, J=1.4, 0.7 Hz, 3H); $^{13}$C NMR (101 MHz, CDCl$_3$) δ 155.9, 148.5, 144.1, 138.7, 131.9, 129.4, 123.6, 122.5, 121.0, 64.7, 55.1, 16.4; IR (Neat Film, NaCl) 3108, 3026, 2969, 2868, 1750, 1530, 1443, 1384, 1353, 1279, 1096, 994, 949, 930, 876, 788, 736, 682 cm$^{-1}$; HRMS (FAB+) m/z calc'd for C$_{12}$H$_{14}$O$_5$N [M+H]$^+$: 252.0872, found 252.0884.

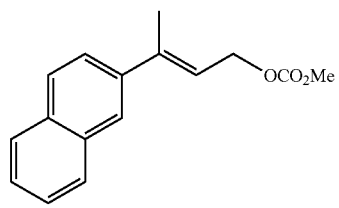

(E)-methyl (3-(Naphthalen-2-yl)but-2-en-1-yl) carbonate (6i)

Carbonate 6i was prepared from methyl (E)-3-(naphthalen-2-yl)but-2-enoate (Gürtler, C.; Buchwald, S. L. *Chem. Eur. J.* 1999, 5, 3107-12) according to Representative Procedure #2 and isolated by silica gel flash column chromatography (5% EtOAc/hexanes) as a colorless oil (0.26 g, 51% yield): $^1$H NMR (400 MHz, CDCl$_3$) δ 7.86-7.77 (m, 4H), 7.58 (dd, J=8.6, 1.9 Hz, 1H), 7.52-7.42 (m, 2H), 6.12-6.05 (m, 1H), 4.92 (dq, J=7.0, 0.7 Hz, 2H), 3.82 (s, 3H), 2.29-2.22 (m, 3H); $^{13}$C NMR (101 MHz, CDCl$_3$) δ 156.0, 140.9, 139.7, 133.4, 133.0, 128.3, 128.0, 127.7, 126.4, 126.1, 124.9, 124.3, 121.3, 65.2, 55.0, 16.5; IR (Neat Film, NaCl) 3057, 2952, 1752, 1740, 1596, 1467, 1442, 1382, 1248, 997, 941, 818, 794, 740 cm$^{-1}$; HRMS (FAB+) m/z calc'd for C$_{16}$H$_{16}$O$_3$ [M]$^+$: 256.1100, found 256.1095.

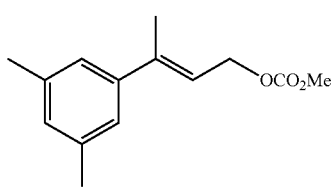

(E)-3-(3,5-Dimethylphenyl)but-2-en-1-yl methyl carbonate (6k)

Carbonate 6k was prepared from methyl (E)-3-(3,5-dimethylphenyl)but-2-enoate (Sano, S.; Yokoyama, K.; Shiro, M.; Nagao, Y. *Chem. Pharm. Bull.* 2002, 50, 706-09) according to Representative Procedure #2 and isolated by silica gel flash column chromatography (5% EtOAc/hexanes) as a colorless oil (0.32 g, 86% yield): $^1$H NMR (400 MHz, CDCl$_3$) δ 7.02 (dt, J=1.6, 0.8 Hz, 2H), 6.93 (td, J=1.6, 0.8 Hz, 1H), 5.96-5.82 (m, 1H), 4.84 (dd, J=7.0, 0.8 Hz, 2H), 3.80 (s, 3H), 2.31 (d, J=0.7 Hz, 6H), 2.15-2.06 (m, 3H); $^{13}$C NMR (101 MHz, CDCl$_3$) δ 156.0, 142.6, 141.5, 137.9, 129.4, 123.9, 120.4, 65.1, 54.9, 21.5, 16.5; IR (Neat Film, NaCl) 2956, 2918, 2862, 1748, 1601, 1443, 1376, 1335, 1262, 944, 905, 849, 792, 699 cm$^{-1}$; HRMS (FAB+) m/z calc'd for C$_{14}$H$_{18}$O$_3$ [M]$^+$: 234.1256, found 234.1252.

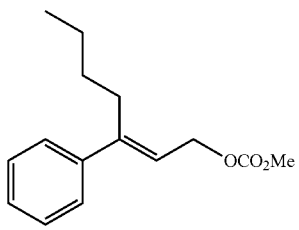

(E)-Methyl (3-phenylhept-2-en-1-yl) carbonate (8b)

Carbonate 8b was prepared from ethyl (E)-3-phenylhept-2-enoate (Ho Oh, C.; Jung, H. H.; Kim, K. S.; Kim, N. *Angew. Chem. Int. Ed.* 2003, 42, 805-08) according to Representative Procedure #2 and isolated by silica gel flash column chromatography (5% EtOAc/hexanes) as a colorless oil (0.31 g, 58% yield): $^1$H NMR (400 MHz, CDCl$_3$) δ 7.48-7.27 (m, 5H), 5.89-5.71 (m, 1H), 4.84 (d, J=7.0 Hz, 2H), 3.80 (s, 3H), 2.73-2.46 (m, 2H), 1.41-1.24 (m, 4H), 1.06-0.73 (m, 3H); $^{13}$C NMR (101 MHz, CDCl$_3$) δ 156.0, 146.6, 142.0, 128.4, 127.6, 126.6, 121.1, 65.0, 55.0, 31.2, 30.2, 22.7, 14.0; IR (Neat Film, NaCl) 3034, 2957, 2872, 1748, 1644, 1599, 1493, 1444, 1378, 1344, 1262, 1129, 941, 792, 766, 698 cm$^{-1}$; HRMS (FAB+) m/z calc'd for C$_{15}$H$_{20}$O$_3$ [M]$^+$: 248.1412, found 248.1424.

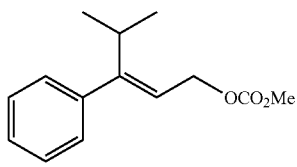

(E)-Methyl (4-methyl-3-phenylpent-2-en-1-yl) carbonate (8c)

Carbonate 8c was prepared from ethyl (E)-4-methyl-3-phenylpent-2-enoate (Bernasconi, M.; Ramella, V.; Tosatti, P.; Pfaltz, A. *Chem. Eur. J.* 2014, 20, 2440-44) according to Representative Procedure #2 and isolated by silica gel flash column chromatography (5% EtOAc/hexanes) as a colorless oil (0.17 g, 17% yield): $^1$H NMR (400 MHz, CDCl$_3$) δ 7.37-7.27 (m, 3H), 7.11-7.02 (m, 2H), 5.61 (td, J=7.0, 1.3 Hz, 1H), 4.46 (dd, J=7.0, 0.8 Hz, 2H), 3.75 (s, 3H), 2.66-2.54 (m, 1H), 1.03 (d, J=6.8 Hz, 6H); $^{13}$C NMR (101 MHz, CDCl$_3$) δ 155.8, 154.0, 139.7, 128.5, 128.2, 127.3, 117.8, 66.1, 54.8, 36.0, 21.5; IR (Neat Film, NaCl) 2961, 2872, 1749, 1492, 1442, 1263, 942, 792, 771, 703 cm$^{-1}$; HRMS (FAB+) m/z calc'd for C$_{14}$H$_{19}$O$_3$ [M+H]$^+$: 235.1334, found 235.1344.

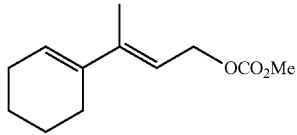

(E)-3-(Cyclohex-1-en-1-yl)but-2-en-1-yl methyl carbonate (8e)

Carbonate 8e was prepared from ethyl (E)-3-(cyclohex-1-en-1-yl)but-2-enoate (Bensel, N.; Höhn, J.; Marschall, H.; Weyerstahl, P. *Eur. J. Inorg. Chem.* 1979, 112, 2256-77) according to Representative Procedure #2 and isolated by silica gel flash column chromatography (5% EtOAc/hexanes) as a colorless oil (0.25 g, 73% yield): $^1$H NMR (400 MHz, CDCl$_3$) δ 6.00-5.92 (m, 1H), 5.68-5.55 (m, 1H), 4.79 (d, J=7.0 Hz, 2H), 3.78 (s, 3H), 2.16 (ddd, J=12.0, 5.9, 3.7 Hz, 4H), 1.85 (d, J=1.1 Hz, 3H), 1.73-1.49 (m, 4H); $^{13}$C NMR (101 MHz, CDCl$_3$) δ 156.0, 141.2, 137.0, 126.0, 116.8, 65.5, 54.9, 26.1, 25.8, 23.0, 22.3, 14.1; IR (Neat Film, NaCl) 2929, 2859, 1749, 1638, 1443, 1263, 1119, 940, 792 cm$^{-1}$; HRMS (FAB+) m/z calc'd for C$_{12}$H$_{18}$O$_3$ [M]$^+$: 210.1256, found 210.1252.

General Procedure for Optimization of the Ir-Catalyzed Allylic Alkylation (Table 1)

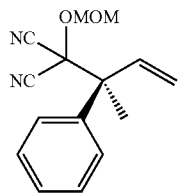

(S)-2-(Methoxymethoxy)-2-(2-phenylbut-3-en-2-yl) malononitrile (3)

In a nitrogen-filled glove box, to a 1 dram vial (vial A) equipped with a stir bar was added [Ir(cod)Cl]$_2$ (1.3 mg, 0.0020 mmol, 2 mol %), ligand (S$_a$)-L3 (2.5 mg, 0.0042 mmol, 4.2 mol %), TBD (1.4 mg, 0.010 mmol, 10 mol %), and THF (0.5 mL). Vial A was stirred at 25° C. (ca. 10 min) while another 1 dram vial (vial B) was charged with MAC nucleophile 1 (0.10 mmol or 0.20 mmol, as specified), THF (0.5 mL), and the Lewis acid additive (200 mol %). The pre-formed catalyst solution (vial A) was then transferred to vial B followed immediately by carbonate 2 (0.20 mmol, 0.10 mmol, or 0.12 mmol, as specified). The vial was sealed and stirred at 60° C. After 18 h, the vial was removed from the glove box and filtered through a pad of silica, rinsing with EtOAc. The crude mixture was concentrated and 1,2,4,5-tetrachloro-3-nitrobenzene (0.10 mmol in 0.5 mL CDCl$_3$) was added. The NMR yield (measured in reference to 1,2,4,5-tetrachloro-3-nitrobenzene δ 7.74 ppm (s, 1H)) was determined by $^1$H NMR analysis of the crude mixture. The residue was purified by preparatory TLC (15% EtOAc/hexanes) to afford MAC adduct product 3 as a colorless oil. For the purposes of characterization, product 3 was further purified by preparatory HPLC (20% EtOAc/hexanes, Viridis SFC 2-Ethylpyridine 5 μm column, flow rate=1.5 mL/min; λ=230 nm): 94% ee (entry 9); [α]$_D^{25}$+11.7 (c 0.07, CHCl$_3$) (entry 9); $^1$H NMR (400 MHz, CDCl$_3$) δ 7.61-7.54 (m, 2H), 7.42-7.32 (m, 3H), 6.51 (dd, J=17.4, 11.0 Hz, 1H), 5.59-5.34 (m, 2H), 5.02 (s, 2H), 3.42 (s, 3H), 1.84 (s, 3H); $^{13}$C NMR (101 MHz, CDCl$_3$) δ 138.3, 137.6, 129.0, 128.57, 238.55, 128.3, 125.2, 119.2, 112.8, 112.7, 96.7, 73.9, 57.5, 52.8, 20.9; IR (Neat Film, NaCl) 3062, 2957, 2896, 2242, 2189, 1750, 1492, 1445, 1358, 1268, 1161, 1108, 1030, 930, 751, 698 cm$^{-1}$; HRMS (ESI+) m/z calc'd for C$_{15}$H$_{17}$N$_2$O$_2$ [M+H]$^+$: 257.1290, found 257.1313; HPLC conditions: 1% IPA, 1.0 mL/min, Chiralpak IC column, λ=210 nm, t$_R$ (min): major=13.303, minor=17.243.

General Procedure for the Enantioenriched Carboxylic Acid Synthesis

Note: that the absolute configuration was determined only for compound 7h via x-ray crystallographic analysis. The absolute configuration for all other products has been inferred by analogy. For respective HPLC and SFC conditions, please refer to Table S1.

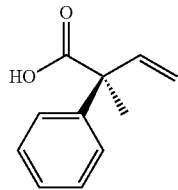

(S)-2-Methyl-2-phenylbut-3-enoic acid (7a)

In a nitrogen-filled glove box, to a 1 dram vial (vial A) equipped with a stir bar was added [Ir(cod)Cl]$_2$ (2.7 mg, 0.0040 mmol, 2 mol %), ligand (S$_a$)-L3 (4.9 mg, 0.0084 mmol, 4.2 mol %), TBD (2.8 mg, 0.020 mmol, 10 mol %), and THF (1 mL). Vial A was stirred at 25° C. (ca. 10 min) while another 1 dram vial (vial B) was charged with MAC nucleophile 1 (25 mg, 0.20 mmol, 100 mol %), THF (1 mL), and BEt$_3$ (400 μL, 1M in hexanes). The pre-formed catalyst solution (vial A) was then transferred to vial B followed immediately by carbonate 2 (83 mg, 0.40 mmol, 200 mol %). The vial was sealed and stirred at 60° C. After 18 h or 48 h, the vial was removed from the glove box, transferred to a 20 mL vial with CH$_2$Cl$_2$, and concentrated. The crude material was heated at 80° C. in 6M HCl (4 mL) for 18 h. Whereupon, the reaction mixture was cooled to 0° C. and basified with 6M NaOH (4.5 mL). The aqueous layer was extracted with CH$_2$Cl$_2$ (4×8 mL). The combined organic layers were washed with 2M NaOH (8 mL). The combined aqueous layers were acidified with concentrated HCl, extracted with CH$_2$Cl$_2$ (4×8 mL), dried over Na$_2$SO$_4$, and concentrated under reduced pressure at 0° C. to give the product 7a as a colorless solid (27 mg, 77% yield): 95% ee; [α]$_D^{25}$+13.5 (c 1.3, CHCl$_3$); HPLC conditions: 2% IPA, 1.0 mL/min, Chiralpak AD-H column, λ=210 nm, t$_R$ (min): major=12.198, minor=11.426. Characterization data match those reported in the literature (Takaya, J.; Iwasawa, N. J. Am. Chem. Soc. 2008, 130, 15254-15255). Please note Compounds 7i, 7j, 7k, and 9a-9g were prepared at the same concentration with double catalyst loadings.

Spectroscopic Data for the Enantioenriched Carboxylic Acids

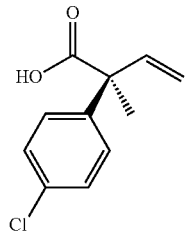

(S)-2-(4-Chlorophenyl)-2-methylbut-3-enoic acid (7b)

Product 7b was prepared according to the general procedure to give a pale yellow oil (33 mg, 80% yield): 93% ee; [α]$_D^{25}$+8.1 (c 1.8, CHCl$_3$); $^1$H NMR (400 MHz, CDCl$_3$) δ 7.38-7.24 (m, 4H), 6.38 (dd, J=17.5, 10.7 Hz, 1H), 5.44-5.16 (m, 2H), 1.66 (s, 3H); $^{13}$C NMR (101 MHz, CDCl$_3$) δ 180.4, 141.1, 140.1, 133.3, 128.7, 128.3, 116.1, 53.3, 23.3; IR (Neat Film, NaCl) 3089, 2987, 2645, 2539, 1705, 1493, 1400, 1282, 1097, 1014, 928, 826, 755 cm$^{-1}$; HRMS (FAB+) m/z calc'd for C$_{11}$H$_{12}$O$_2$Cl [M+H]$^+$: 211.0526, found 211.0528; HPLC conditions: 2% IPA, 1.0 mL/min, Chiralpak AD-H column, λ=210 nm, t$_R$ (min): major=15.642, minor=14.104.

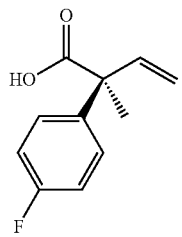

(S)-2-(4-Fluorophenyl)-2-methylbut-3-enoic acid (7c)

Product 7c was prepared according to the general procedure to give a pale yellow oil (35 mg, 90% yield): 90% ee; $[\alpha]_D^{25}$+3.4 (c 1.5, CHCl$_3$); $^1$H NMR (400 MHz, CDCl$_3$) δ 7.46-7.19 (m, 2H), 7.05 (t, J=8.7 Hz, 2H), 6.39 (dd, J=17.5, 10.7 Hz, 1H), 5.42-5.14 (m, 2H), 1.67 (s, 3H); $^{13}$C NMR (101 MHz, CDCl$_3$) δ 180.6, 163.2, 160.7, 140.4, 138.3 (d, J=3.4 Hz), 128.5 (d, J=8.1 Hz), 115.9, 115.5, 115.3, 53.2, 23.5; IR (Neat Film, NaCl) 3088, 2987, 2924, 2642, 1704, 1603, 1510, 1462, 1412, 1277, 1234, 1165, 928, 833, 816, 735 cm$^{-1}$; HRMS (FAB+) m/z calc'd for C$_{11}$H$_{12}$FO$_2$ [M+H]$^+$: 195.0833, found 195.0841; HPLC conditions: 2% IPA, 1.0 mL/min, Chiralpak AD-H column, λ=210 nm, t$_R$ (min): major=15.499, minor=13.811.

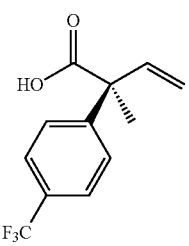 [SMILES: C=C[C@](C)(C(=O)O)c1ccc(C(F)(F)F)cc1]

(S)-2-Methyl-2-(4-(trifluoromethyl)phenyl)but-3-enoic acid (7d)

Product 7d was prepared according to the general procedure to give a pale yellow oil (41 mg, 83% yield): 92% ee; $[\alpha]_D^{25}$-2.2 (c 2.3, CHCl$_3$); $^1$H NMR (400 MHz, CDCl$_3$) δ 7.60 (dt, J=8.1, 0.8 Hz, 2H), 7.45 (dt, J=8.3, 0.8 Hz, 2H), 6.38 (dd, J=17.5, 10.7 Hz, 1H), 5.48-5.09 (m, 2H), 1.68 (s, 3H); $^{13}$C NMR (101 MHz, CDCl$_3$) δ 179.0, 146.6, 139.7, 129.6, 130.0, 129.5, 127.2, 125.6 (q, J=3.7 Hz), 122.8, 116.6, 53.7, 29.9, 23.4; IR (Neat Film, NaCl) 2926, 2649, 1707, 1618, 1413, 1328, 1277, 1167, 1126, 1081, 1016, 930, 940 cm$^{-1}$; HRMS (FAB+) m/z calc'd for C$_{12}$H$_{12}$O$_2$F$_3$ [M+H]$^+$: 245.0789, found 245.0794; SFC conditions: 2% IPA, 2.5 mL/min, Chiralpak AD-H column, λ=210 nm, t$_R$ (min): major=13.592, minor=15.745.

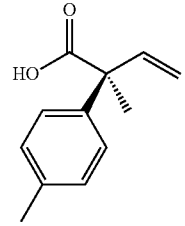

(S)-2-Methyl-2-(p-tolyl)but-3-enoic acid (7e)

Product 7e was prepared according to the general procedure to give a pale yellow oil (24 mg, 63% yield): 94% ee; $[\alpha]_D^{25}$+4.6 (c 0.8, CHCl$_3$); $^1$H NMR (400 MHz, CDCl$_3$) δ 7.42-7.01 (m, 4H), 6.40 (dd, J=17.5, 10.7 Hz, 1H), 5.59-5.08 (m, 2H), 2.34 (s, 3H), 1.64 (s, 3H); $^{13}$C NMR (101 MHz, CDCl$_3$) δ 181.0, 140.7, 139.8, 137.0, 129.3, 126.6, 115.4, 53.3, 23.3, 21.1; IR (Neat Film, NaCl) 2986, 1702, 1636, 1512, 1457, 1412, 1276, 1191, 1132, 1077, 1020, 925, 815, 730 cm$^{-1}$; HRMS (ESI−) m/z calc'd for C$_{12}$H$_{13}$O$_2$ [M−H]$^-$: 189.0916, found 189.0903; HPLC conditions: 2% IPA, 1.0 mL/min, Chiralpak AD-H column, λ=210 nm, t$_R$ (min): major=15.393, minor=14.288.

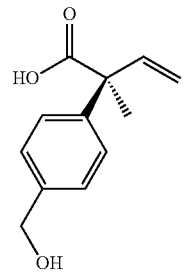

(S)-2-(4-(Hydroxymethyl)phenyl)-2-methylbut-3-enoic acid (7f)

Product 7f was prepared according to the general procedure and isolated by preparatory TLC (30% acetone/hexanes) to give a colorless solid (21 mg, 51% yield): 95% ee; $[\alpha]_D^{25}$+3.4 (c 0.5, CHCl$_3$); $^1$H NMR (400 MHz, CDCl$_3$) δ 7.33 (q, J=8.2 Hz, 4H), 6.37 (dd, J=17.5, 10.7 Hz, 1H), 5.39-5.10 (m, 2H), 4.57 (s, 2H), 1.63 (s, 3H); $^{13}$C NMR (101 MHz, CDCl$_3$) δ 180.1, 143.2, 140.4, 136.4, 128.8, 127.2, 115.8, 53.6, 45.9, 23.4; IR (Neat Film, NaCl) 2985, 2927, 2642, 1703, 1636, 1512, 1460, 1268, 1182, 1076, 926, 836, 731, 683 cm$^{-1}$; HRMS (FAB+) m/z calc'd for C$_{12}$H$_{15}$O$_3$ [M+H]$^+$: 207.1021, found 207.1025; HPLC conditions: 2% IPA, 1.0 mL/min, Chiralpak AD-H column, λ=210 nm, t$_R$ (min): major=15.258, minor=14.667.

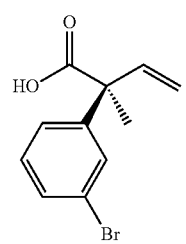

(S)-2-(3-Bromophenyl)-2-methylbut-3-enoic acid (7g)

Product 7g was prepared according to the general procedure to give a pale yellow oil (35 mg, 69% yield): 92% ee; $[\alpha]_D^{25}$-2.6 (c 1.8, CHCl$_3$); $^1$H NMR (400 MHz, CDCl$_3$) δ 7.47 (t, J=1.9 Hz, 1H), 7.41 (ddd, J=7.6, 1.9, 1.2 Hz, 1H), 7.29-7.18 (m, 2H), 6.35 (dd, J=17.5, 10.7 Hz, 1H), 5.42-5.09 (m, 2H), 1.65 (s, 3H); $^{13}$C NMR (101 MHz, CDCl$_3$) δ 179.7, 145.0, 139.8, 130.5, 130.2, 129.9, 125.5, 122.8, 116.4, 53.5, 23.3; IR (Neat Film, NaCl) 2987, 2644, 1705, 1593, 1566, 1475, 1413, 1280, 1129, 1070, 997, 928, 785, 760, 700 cm$^{-1}$; HRMS (ESI−) m/z calc'd for C$_{11}$H$_{10}$O$_2$Br [M−H]$^-$: 252.9864, found 252.9864; HPLC conditions: 2% IPA, 1.0 mL/min, Chiralpak AD-H column, λ=210 nm, $t_R$ (min): major=15.217, minor=14.439.

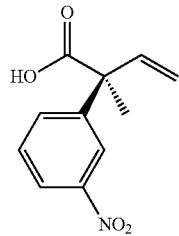 [SMILES: C=C[C@](C)(C(=O)O)c1cccc([N+](=O)[O-])c1]

(S)-2-Methyl-2-(3-nitrophenyl)but-3-enoic acid (7h)

Product 7h was prepared according to the general procedure to give a colorless solid (41 mg, 93% yield): 87% ee; $[\alpha]_D^{25}$+94.5 (c 3.4, CHCl$_3$); $^1$H NMR (400 MHz, CDCl$_3$) δ 8.22 (t, J=2.0 Hz, 1H), 8.15 (ddd, J=8.2, 2.2, 1.0 Hz, 1H), 7.69 (ddd, J=7.9, 1.9, 1.1 Hz, 1H), 7.53 (t, J=8.0 Hz, 1H), 6.38 (dd, J=17.5, 10.7 Hz, 1H), 5.59-5.11 (m, 2H), 1.72 (s, 3H); $^{13}$C NMR (101 MHz, CDCl$_3$) δ 179.6, 148.5, 144.7, 139.2, 133.3, 129.6, 122.5, 122.1, 117.2, 53.7, 23.4; IR (Neat Film, NaCl) 3089, 2988, 2924, 2641, 1707, 1530, 1351, 1276, 1106, 929, 808, 738, 688 cm$^{-1}$; HRMS (FAB+) m/z calc'd for C$_{11}$H$_{12}$O$_4$N [M+H]$^+$: 222.0766, found 222.0769; HPLC conditions: 3% IPA, 1.0 mL/min, Chiralpak AD-H column, λ=210 nm, $t_R$ (min): major=24.060, minor=20.907.

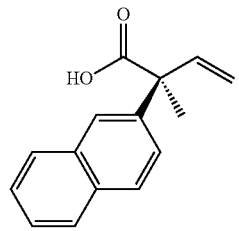 [SMILES: C=C[C@](C)(C(=O)O)c1ccc2ccccc2c1]

(S)-2-Methyl-2-(naphthalen-2-yl)but-3-enoic acid (7i)

Product 7i was prepared according to the general procedure to give a pale yellow oil (30 mg, 66% yield): 92% ee; $[\alpha]_D^{25}$+7.8 (c 0.6, CHCl$_3$); $^1$H NMR (400 MHz, CDCl$_3$) δ 7.91-7.72 (m, 4H), 7.55-7.39 (m, 3H), 6.52 (dd, J=17.5, 10.7 Hz, 1H), 5.57-5.11 (m, 2H), 1.77 (s, 3H); $^{13}$C NMR (101 MHz, CDCl$_3$) δ 180.9, 140.5, 140.0, 133.3, 132.5, 128.3, 128.2, 127.6, 126.3, 126.2, 125.3, 125.2, 116.0, 53.9, 23.4; IR (Neat Film, NaCl) 3057, 2984, 1701, 1506, 1458, 1411, 1274, 1182, 1128, 1102, 925, 856, 816, 747 cm$^{-1}$; HRMS (FAB+) m/z calc'd for C$_{15}$H$_{14}$O$_2$ [M]$^+$: 226.0994, found 226.0992; HPLC conditions: 2% IPA, 1.0 mL/min, Chiralpak AD-H column, λ=210 nm, $t_R$ (min): major=28.272, minor=24.870.

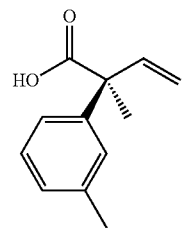

(S)-2-Methyl-2-(m-tolyl)but-3-enoic acid (7j)

Product 7j was prepared according to the general procedure to give a pale yellow oil (26 mg, 68% yield): 93% ee; $[\alpha]_D^{25}$+5.2 (c 1.6, CHCl$_3$); $^1$H NMR (400 MHz, CDCl$_3$) δ 7.25-7.04 (m, 4H), 6.40 (dd, J=17.5, 10.7 Hz, 1H), 5.45-5.08 (m, 2H), 2.44-2.20 (m, 3H), 1.65 (s, 3H); $^{13}$C NMR (101 MHz, CDCl$_3$) δ 180.2, 142.7, 140.6, 138.3, 128.5, 128.1, 127.3, 123.7, 115.6, 53.6, 23.3, 21.7; IR (Neat Film, NaCl) 2984, 2923, 2648, 1703, 1606, 1459, 1411, 1275, 1178, 1127, 1002, 926, 785, 703 cm$^{-1}$; HRMS (FAB+) m/z calc'd for Cl$_2$H$_{15}$O$_2$ [M+H]$^+$: 191.1072, found 191.1074; HPLC conditions: 2% IPA, 1.0 mL/min, Chiralpak AD-H column, λ=210 nm, $t_R$ (min): major=13.800, minor=12.388.

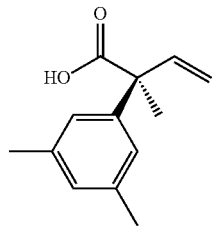

(S)-2-(3,5-Dimethylphenyl)-2-methylbut-3-enoic acid (7k)

Product 7k was prepared according to the general procedure and isolated by preparatory TLC (30% acetone/hexanes) to give a colorless oil (13 mg, 32% yield): 85% ee; $[\alpha]_D^{25}$-40.6 (c 0.1, CHCl$_3$); $^1$H NMR (400 MHz, CDCl$_3$) δ 6.94 (d, J=8.5 Hz, 3H), 6.42 (dd, J=17.4, 10.6 Hz, 1H), 5.45-5.08 (m, 2H), 2.33 (s, 6H), 1.65 (s, 3H); $^{13}$C NMR (101 MHz, CDCl$_3$) δ 180.5, 142.8, 140.8, 138.1, 129.0, 124.4, 115.3, 53.6, 23.3, 21.6; IR (Neat Film, NaCl) 2983, 2919, 2639, 1700, 1602, 1411, 1279, 1125, 923, 848, 708 cm$^{-1}$;

HRMS (FAB+) m/z calc'd for $C_{13}H_{17}O_2$ [M+H]$^+$: 205.1229, found 205.1233; HPLC conditions: 2% IPA, 1.0 mL/min, Chiralpak AD-H column, λ=210 nm, $t_R$ (min): major=11.107, minor=10.064. Please note an HMBC has been included due to the low intensity of the carbonyl $^{13}$C shift at δ 180.5.

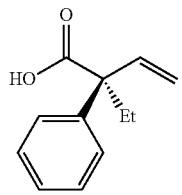

(S)-2-Ethyl-2-phenylbut-3-enoic acid (9a)

Product 9a was prepared according to the general procedure and isolated by preparatory TLC (30% acetone/hexanes) to give a a colorless oil (23 mg, 61% yield): 92% ee; $[\alpha]_D^{25}$+17.4 (c 0.4, CHCl$_3$); $^1$H NMR (400 MHz, CDCl$_3$) δ 7.38 7.22 (m, 5H), 6.36 (dd, J=17.7, 10.9 Hz, 1H), 5.35 (d, J=10.7 Hz, 1H), 5.09 (d, J=17.6 Hz, 1H), 2.36-2.00 (m, 2H), 0.87 (t, J=7.2 Hz, 3H).; $^{13}$C NMR (101 MHz, CDCl$_3$) δ 180.1, 141.3, 139.1, 128.4, 127.6, 127.2, 116.9, 58.0, 29.4, 9.4; IR (Neat Film, NaCl) 3060, 2970, 2928, 2636, 1702, 1495, 1448, 1407, 1381, 1261, 1083, 924, 761, 700 cm$^{-1}$; HRMS (FAB+) m/z calc'd for $Cl_2H_{15}O_2$ [M+H]$^+$: 191.1072, found 191.1071; HPLC conditions: 1.5% IPA, 1.0 mL/min, two Chiralpak AD-H columns in series, λ=210 nm, $t_R$ (min): major=46.253, minor=47.271.

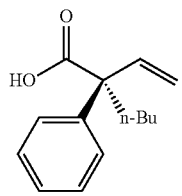

(S)-2-Phenyl-2-vinylhexanoic acid (9b)

Product 9b was prepared according to the general procedure and isolated by preparatory TLC (30% acetone/hexanes) to give a colorless oil (6 mg, 14% yield): 95% ee; $[\alpha]_D^{25}$-106.0 (c 0.07, CHCl$_3$); $^1$H NMR (400 MHz, CDCl$_3$) δ 7.40-7.29 (m, 5H), 6.38 (dd, J=17.6, 10.9 Hz, 1H), 5.32 (dd, J=10.9, 0.9 Hz, 1H), 5.06 (dd, J=17.6, 0.9 Hz, 1H), 2.28-1.98 (m, 2H), 1.44-1.14 (m, 4H), 0.87 (t, J=7.2 Hz, 3H); $^{13}$C NMR (101 MHz, CDCl$_3$) δ 178.4, 141.6, 139.7, 128.4, 127.5, 127.1, 116.6, 57.5, 36.5, 27.0, 23.4, 14.1; IR (Neat Film, NaCl) 2956, 2920, 2851, 1734, 1706, 1466, 1378, 1260, 1098, 925, 800, 722, 700 cm$^{-1}$; HRMS (FAB+) m/z calc'd for $C_{14}H_{19}O_2$ [M+H]$^+$: 219.1385, found 219.1291; SFC conditions: 5% IPA, 2.5 mL/min, Chiralpak AD-H column, λ=210 nm, $t_R$ (min): major=10.646, minor=11.952.

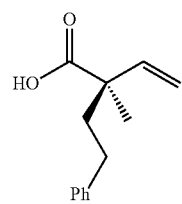

(R)-2-Methyl-2-phenethylbut-3-enoic acid (9f)

Product 9f was prepared according to the general procedure and isolated by preparatory TLC (33% acetone/hexanes) to give a colorless oil (13 mg, 32% yield): 3% ee; $[\alpha]_D^{25}$-12.1 (c 0.7, CHCl$_3$); $^1$H NMR (400 MHz, CDCl$_3$) δ 7.44-7.04 (m, 5H), 6.10 (dd, J=17.6, 10.7 Hz, 1H), 5.21 (dd, J=14.0, 3.3 Hz, 2H), 2.60 (dt, J=11.0, 4.9 Hz, 2H), 2.33-1.79 (m, 2H), 1.40 (s, 3H); $^{13}$C NMR (101 MHz, CDCl$_3$) δ 182.0, 142.0, 140.9, 128.54, 128.49, 126.1, 114.7, 48.7, 41.1, 31.2, 20.7; IR (Neat Film, NaCl) 3026, 2927, 1702, 1496, 1454, 1380, 1264, 1097, 925, 748, 700 cm$^{-1}$; HRMS (FAB+) m/z calc'd for $C_{13}H_{17}O_2$ [M+H]$^+$: 267.1385, found 267.1376; HPLC conditions: 2% IPA, 1.0 mL/min, Chiralpak AD-H column, λ=210 nm, $t_R$ (min): major=18.485, minor=14.652. Please note an HMBC has been included due to the low intensity of the carbonyl $^{13}$C shift at δ 182.0.

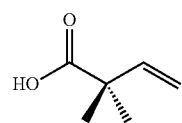

2,2-Dimethylbut-3-enoic acid (9g)

Product 9g was prepared according to the general procedure to give a colorless oil (15 mg, 63% yield). Characterization data match those reported in the literature (Duong, H. A.; Huleatt, P. B.; Tan. Q.-W.; Shuying, E. L. *Org. Lett.* 2013, 15, 4034-37).

Determination of Enantiomeric Excess

Note: racemic products were synthesized using racemic L3.

TABLE 5

| | | | Retention time of major isomer | Retention time of minor isomer | |
|---|---|---|---|---|---|
| Entry | Product | Assay Conditions | (min) | (min) | % ee |
| 7 | *structure: 2-(4-(hydroxymethyl)phenyl)-2-methylbut-3-enoic acid* | HPLC Chiralpak AD-H 2% IPA isocratic, 1 mL/min | 15.258 | 14.667 | 95% |
| 8 | *structure: 2-(3-bromophenyl)-2-methylbut-3-enoic acid* | HPLC Chiralpak AD-H 2% IPA Isocratic, 1 mL/min | 15.217 | 14.439 | 92% |
| 9 | *structure: 2-methyl-2-(3-nitrophenyl)but-3-enoic acid* | HPLC Chiralpak AD-H 3% IPA isocratic, 1 mL/min | 24.060 | 20.907 | 87% |
| 10 | *structure: 2-methyl-2-(naphthalen-2-yl)but-3-enoic acid* | HPLC Chiralpak AD-H 2% IPA isocratic, 1 mL/min | 28.272 | 24.870 | 92% |
| 11 | *structure: 2-methyl-2-(m-tolyl)but-3-enoic acid* | HPLC Chiralpak AD-H 2% IPA Isocratic, 1 mL/min | 13.800 | 12.388 | 93% |
| 12 | *structure: 2-(3,5-dimethylphenyl)-2-methylbut-3-enoic acid* | HPLC Chiralpak AD-H 2% IPA Isocratic, 1 mL/min | 11.107 | 10.064 | 85% |

TABLE 5-continued

Determination of Enantiomeric Excess

| Entry | Product | Assay Conditions | Retention time of major isomer (min) | Retention time of minor isomer (min) | % ee |
|---|---|---|---|---|---|
| 13 | (structure: HOOC-C(Et)(vinyl)-Ph) | HPLC two Chiralpak AD-H in series 1.5% IPA Isocratic, 1 mL/min | 46.253 | 47.271 | 92% |
| 14 | (structure: HOOC-C(n-Bu)(vinyl)-Ph) | SFC Chiralpak AD-H 5% IPA Isocratic, 2.5 mL/min | 10.646 | 11.952 | 95% |
| 15 | (structure: HOOC-C(Me)(vinyl)-CH₂CH₂Ph) | HPLC Chiralpak AD-H 2% IPA isocratic, 1 mL/min | 18.485 | 14.652 | 3% |

Experimental Procedures and Spectroscopic Data for the One-Pot Syntheses of Carboxylic Acid Derivatives

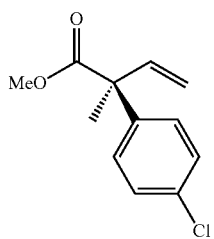

Methyl (S)-2-(4-chlorophenyl)-2-methylbut-3-enoate (10)

In a nitrogen-filled glove box, to a scintillation vial (vial A) equipped with a stir bar was added [Ir(cod)Cl]$_2$ (13 mg, 0.02 mmol, 2 mol %), ligand (S$_a$)-L3 (25 mg, 0.042 mmol, 4.2 mol %), TBD (14 mg, 0.10 mmol, 10 mol %), and THF (5 mL). Vial A was stirred at 25° C. (ca. 10 min) while another scintillation vial (vial B) was charged with MAC nucleophile 1 (126 mg, 1.0 mmol, 100 mol %), THF (5 mL), and BEt$_3$ (2.0 mL, 1M in hexanes). The pre-formed catalyst solution (vial A) was then transferred to vial B followed immediately by carbonate 6b (480 mg, 2.0 mmol, 200 mol %). The vial was sealed and stirred at 60° C. After 18 h, the vial was removed from the glove box and the reaction mixture was concentrated under reduced pressure.

To the vial of crude MAC adduct equipped with a stir bar and septum cap was added 1:1 AcOH/DME (2 mL, 0.5 M) and CSA (0.26 g, 1.1 mmol, 1.1 equiv) under a nitrogen atmosphere. The reaction was heated to 60° C. for 6 h, whereupon the reaction mixture was cooled to ambient temperature, diluted with anhydrous MeOH (2.8 mL), and cooled to −40° C. A solution of 1:1 MeOH/Et$_3$N (5.6 mL, 20.1 equiv of Et$_3$N) was added dropwise over 10 min. The reaction mixture was allowed to warm to ambient temperature over 18 h, whereupon the reaction was slowly quenched with saturated NH$_4$Cl aqueous solution (5 mL). The aqueous layer was then extracted with CH$_2$Cl$_2$ (3×10 mL) and the combined organic layers were washed with brine (10 mL), dried over Na$_2$SO$_4$, and concentrated under reduced pressure at 0° C. The crude residue was purified by silica gel flash column chromatography (10% EtOAc/hexanes) to give methyl ester 10 as a colorless oil (0.20 g, 88% yield): $[\alpha]_D^{25}$+1.5 (c 0.8, CHCl$_3$); $^1$H NMR (400 MHz, CDCl$_3$) δ 7.41-6.99 (m, 4H), 6.35 (dd, J=17.5, 10.7 Hz, 1H), 5.48-5.00 (m, 2H), 3.70 (s, 3H), 1.62 (s, 3H); $^{13}$C NMR (101 MHz, CDCl$_3$) δ 175.0, 142.0, 140.6, 132.9, 128.7, 128.1, 115.6, 53.5, 52.7, 23.7; IR (Neat Film, NaCl) 2986, 2952, 1734, 1637, 1493, 1459, 1246, 1181, 1123, 1098, 1014, 926, 828, 757 cm$^{-1}$; HRMS (FAB+) m/z calc'd for Cl$_2$H$_{13}$ClO$_2$ [M+]$^+$: 224.0604, found 224.0621.

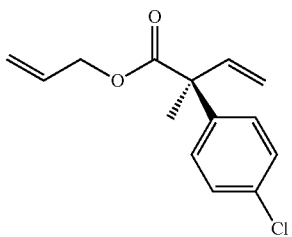 [SMILES: C=CCOC(=O)[C@@](C)(C=C)c1ccc(Cl)cc1]

Allyl (S)-2-(4-chlorophenyl)-2-methylbut-3-enoate (11)

In a nitrogen-filled glove box, to a 1 dram vial (vial A) equipped with a stir bar was added [Ir(cod)Cl]$_2$ (2.7 mg, 0.0040 mmol, 2 mol %), ligand (S$_a$)-L3 (4.9 mg, 0.0084 mmol, 4.2 mol %), TBD (2.8 mg, 0.020 mmol, 10 mol %), and THF (1 mL). Vial A was stirred at 25° C. (ca. 10 min) while another 1 dram vial (vial B) was charged with MAC nucleophile 1 (25 mg, 0.20 mmol, 100 mol %), THF (1 mL), and BEt$_3$ (400 µL, 1M in hexanes). The pre-formed catalyst solution (vial A) was then transferred to vial B followed immediately by carbonate 6b (96 mg, 0.40 mmol, 200 mol %). The vial was sealed and stirred at 60° C. After 18 h, the vial was removed from the glove box, transferred to a 20 mL vial with CH$_2$Cl$_2$, and concentrated.

To the vial of crude MAC adduct equipped with a stir bar and septum cap was added 1:1 AcOH/DME (0.4 mL, 0.5 M) and CSA (51 mg, 0.22 mmol, 1.1 equiv) under a nitrogen atmosphere. The reaction was heated to 60° C. for 6 h, whereupon the reaction mixture was cooled to ambient temperature, diluted with allyl alcohol (0.4 mL), and cooled to 0° C. A solution of 1:1 Et$_3$N/allyl alcohol (1.1 mL, 20.4 equiv of Et$_3$N) was added dropwise over 10 min. The reaction mixture was allowed to warm to ambient temperature over 18 h, whereupon the reaction was slowly quenched with saturated NH$_4$Cl aqueous solution (5 mL). The aqueous layer was then extracted with CH$_2$Cl$_2$ (3×10 mL) and the combined organic layers were washed with brine (10 mL), dried over Na$_2$SO$_4$, and concentrated under reduced pressure at 0° C. The crude residue was purified by preparatory TLC (8% EtOAc/hexanes) to give allyl ester 11 as a colorless oil (37 mg, 74% yield): [α]$_D^{25}$+0.4 (c 2.3, CHCl$_3$); $^1$H NMR (400 MHz, CDCl$_3$) δ 7.35-7.12 (m, 4H), 6.36 (dd, J=17.5, 10.7 Hz, 1H), 5.85 (ddt, J=17.2, 10.5, 5.6 Hz, 1H), 5.38-5.02 (m, 4H), 4.61 (dt, J=5.6, 1.4 Hz, 2H), 1.63 (s, 3H); $^{13}$C NMR (101 MHz, CDCl$_3$) δ 174.1, 142.0, 140.6, 132.9, 131.9, 128.6, 128.1, 118.5, 115.6, 65.9, 53.5, 23.6; IR (Neat Film, NaCl) 3089, 2985, 2930, 2857, 1900, 1734, 1638, 1493, 1236, 1177, 1122, 1097, 1014, 926, 828, 756 cm$^{-1}$; HRMS (FAB+) m/z calc'd for C$_{14}$H$_{16}$O$_2$Cl [M+H]$^+$: 251.0839, found 251.0842.

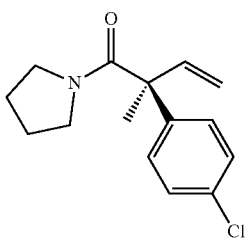 [SMILES: C=C[C@](C)(C(=O)N1CCCC1)c1ccc(Cl)cc1]

(S)-2-(4-Chlorophenyl)-2-methyl-1-(pyrrolidin-1-yl) but-3-en-1-one (12)

In a nitrogen-filled glove box, to a 1 dram vial (vial A) equipped with a stir bar was added [Ir(cod)Cl]$_2$ (2.7 mg, 0.0040 mmol, 2 mol %), ligand (S$_a$)-L3 (4.9 mg, 0.0084 mmol, 4.2 mol %), TBD (2.8 mg, 0.020 mmol, 10 mol %), and THF (1 mL). Vial A was stirred at 25° C. (ca. 10 min) while another 1 dram vial (vial B) was charged with MAC nucleophile 1 (25 mg, 0.20 mmol, 100 mol %), THF (1 mL), and BEt$_3$ (400 µL, 1M in hexanes). The pre-formed catalyst solution (vial A) was then transferred to vial B followed immediately by carbonate 6b (96 mg, 0.40 mmol, 200 mol %). The vial was sealed and stirred at 60° C. After 18 h, the vial was removed from the glove box, transferred to a 20 mL vial with CH$_2$Cl$_2$, and concentrated.

To the vial of crude MAC adduct equipped with a stir bar and septum cap was added 1:1 AcOH/DME (0.4 mL, 0.5 M) and CSA (51 mg, 0.22 mmol, 1.1 equiv) under a nitrogen atmosphere. The reaction was heated to 60° C. for 6 h, whereupon the reaction mixture was cooled to ambient temperature, diluted with CH$_2$Cl$_2$ (0.4 mL), and cooled to −40° C. A solution of 1:1 pyrrolidine/CH$_2$Cl$_2$ (0.67 mL, 20.4 equiv of pyrrolidine) was added dropwise over 10 min then Et$_3$N (0.57 mL, 4.1 mmol, 20.4 equiv). The reaction mixture was allowed to warm to ambient temperature over 18 h, whereupon the reaction was slowly quenched with saturated NH$_4$Cl aqueous solution (5 mL). The aqueous layer was then extracted with CH$_2$Cl$_2$ (3×10 mL) and the combined organic layers were washed with brine (10 mL), dried over Na$_2$SO$_4$, and concentrated under reduced pressure at 0° C. The crude residue was purified by preparatory TLC (30% acetone/hexanes) to give amide 12 as a colorless oil (32 mg, 61% yield): [α]$_D^{25}$-49.5 (c 1.7, CHCl$_3$); $^1$H NMR (400 MHz, CDCl$_3$) δ 7.34-7.28 (m, 2H), 7.21-7.14 (m, 2H), 6.45 (dd, J=17.4, 10.7 Hz, 1H), 5.27 (dd, J=10.7, 0.8 Hz, 1H), 5.10 (dd, J=17.4, 0.8 Hz, 1H), 3.63-3.47 (m, 2H), 2.98 (dt, J=10.6, 6.3 Hz, 1H), 2.52 (dt, J=10.6, 6.7 Hz, 1H), 1.78-1.62 (m, 2H), 1.64-1.55 (m, 5H); $^{13}$C NMR (101 MHz, CDCl$_3$) δ 172.1, 143.2, 139.7, 132.5, 129.0, 127.6, 115.5, 54.3, 47.52, 47.44, 28.4, 26.5, 23.5; IR (Neat Film, NaCl) 2928, 2873, 1742, 1627, 1491, 1396, 1228, 1185, 1096, 1012, 921, 829, 723 cm$^{-1}$; HRMS (FAB+) m/z calc'd for C$_{15}$H$_{19}$ClNO [M+H]$^+$: 264.1155, found 264.1154.

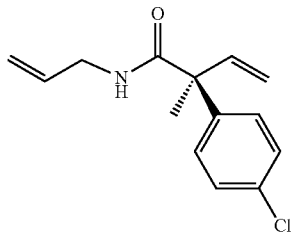 [SMILES: C=CCNC(=O)[C@@](C)(C=C)c1ccc(Cl)cc1]

(S)—N-allyl-2-(4-chlorophenyl)-2-methylbut-3-enamide (13)

In a nitrogen-filled glove box, to a 1 dram vial (vial A) equipped with a stir bar was added [Ir(cod)Cl]$_2$ (2.7 mg, 0.0040 mmol, 2 mol %), ligand (S$_a$)-L3 (4.9 mg, 0.0084 mmol, 4.2 mol %), TBD (2.8 mg, 0.020 mmol, 10 mol %), and THF (1 mL). Vial A was stirred at 25° C. (ca. 10 min) while another 1 dram vial (vial B) was charged with MAC nucleophile 1 (25 mg, 0.20 mmol, 100 mol %), THF (1 mL), and BEt$_3$ (400 µL, 1M in hexanes). The pre-formed catalyst solution (vial A) was then transferred to vial B followed immediately by carbonate 6b (96 mg, 0.40 mmol, 200 mol %). The vial was sealed and stirred at 60° C. After 18 h, the vial was removed from the glove box, transferred to a 20 mL vial with CH$_2$Cl$_2$, and concentrated.

To the vial of crude MAC adduct equipped with a stir bar and septum cap was added 1:1 AcOH/DME (0.4 mL, 0.5 M) and CSA (51 mg, 0.22 mmol, 1.1 equiv) under a nitrogen atmosphere. The reaction was heated to 60° C. for 6 h, whereupon the reaction mixture was cooled to ambient temperature, diluted with allyl amine (0.4 mL), and cooled to 0° C. A solution of 1:1 Et$_3$N/allyl amine (1.1 mL, 20.4 equiv of Et$_3$N) was added dropwise over 10 min. The reaction mixture was allowed to warm to ambient temperature over 18 h, whereupon the reaction was slowly quenched with saturated NH$_4$Cl aqueous solution (5 mL). The aqueous layer was then extracted with CH$_2$Cl$_2$ (3×10 mL) and the combined organic layers were washed with brine (10 mL), dried over Na$_2$SO$_4$, and concentrated under reduced pressure at 0° C. The crude residue was purified by preparatory TLC (30% EtOAc/hexanes) to give allyl amide 13 as a colorless oil (31 mg, 63% yield): $[\alpha]_D^{25}$+10.2 (c 1.6, CHCl$_3$); $^1$H NMR (400 MHz, CDCl$_3$) δ 7.42-7.17 (m, 4H), 6.29 (dd, J=17.4, 10.6 Hz, 1H), 5.90-5.75 (m, 1H), 5.64 (s, 1H), 5.33 (dd, J=10.6, 0.8 Hz, 1H), 5.20-5.03 (m, 3H), 3.96-3.82 (m, 2H), 1.67 (s, 3H); $^{13}$C NMR (101 MHz, CDCl$_3$) δ 174.1, 142.0, 141.8, 134.1, 133.1, 128.9, 128.8, 116.6, 116.5, 54.3, 42.3, 24.6; IR (Neat Film, NaCl) 3341, 3085, 2983, 2931, 1739, 1658, 1520, 1493, 1414, 1270, 1096, 1014, 922, 827, 725, 657 cm$^{-1}$; HRMS (FAB+) m/z calc'd for C$_{14}$H$_{17}$NOCl [M+H]$^+$: 250.0999, found 250.0991.

Experimental Procedures and Spectroscopic Data for the Product Transformations

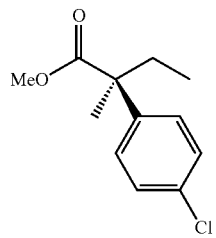

Methyl (S)-2-(4-chlorophenyl)-2-methylbutanoate (14)

To a solution of olefin 10 (13 mg, 0.056 mmol, 1 equiv) in EtOAc (1 mL) was added Pd/C (2.5 mg, 20% w/w). The reaction mixture was sparged with a hydrogen gas (balloon) for 5 minutes and then stirred under a hydrogen atmosphere for 18 h, whereupon the reaction was filtered through celite with EtOAc (5 mL) and concentrated under reduced pressure at 0° C. to give alkyl 14 as a colorless oil (12 mg, 97% yield): $[\alpha]_D^{25}$+3.6 (c 1.2, CHCl$_3$); $^1$H NMR (400 MHz, CDCl$_3$) δ 7.41-7.15 (m, 4H), 3.67 (s, 3H), 2.31-1.80 (m, 2H), 1.53 (s, 3H), 0.83 (t, J=7.4 Hz, 3H); $^{13}$C NMR (101 MHz, CDCl$_3$) δ 176.5, 142.4, 132.6, 128.6, 127.7, 52.3, 50.4, 32.0, 22.2, 9.2; IR (Neat Film, NaCl) 2970, 2880, 1731, 1493, 1457, 1383, 1307, 1238, 1147, 1096, 1012, 824, 756, 720 cm$^{-1}$; HRMS (FAB+) m/z calc'd for C$_{12}$H$_{16}$O$_2$Cl [M+H]$^+$: 227.0839, found 227.0840.

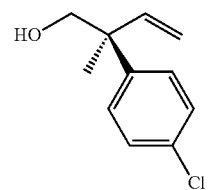

(S)-2-(4-Chlorophenyl)-2-methylbut-3-en-1-ol (15)

DIBAL (0.029 mL, 0.16 mmol, 3 equiv) was added dropwise to a solution of methyl ester 10 (13 mg, 0.056 mmol, 1 equiv) in Et$_2$O (1.0 mL) at 0° C. The mixture was stirred at 0° C. for 2 h, whereupon the reaction was quenched with a saturated Rochelle's salt aqueous solution (1 mL) and stirred for 18 h at ambient temperature. The aqueous layer was then extracted with CH$_2$Cl$_2$ (3×5 mL) and the combined organic layers were washed with brine (5 mL), dried over Na$_2$SO$_4$, and concentrated under reduced pressure at 0° C. The crude residue was purified by preparatory TLC (25% acetone/hexanes) to give alcohol 15 as a colorless oil (8 mg, 73% yield): $[\alpha]_D^{25}$+11.0 (c 0.4, CHCl$_3$). Characterization data match those reported in the literature (Ngai, M.-Y.; Skucas, E.; Krische, M. *J. Org. Lett.* 2008, 10, 2705-08).

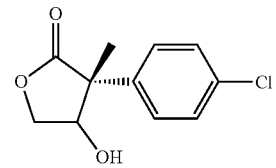

(3S)-3-(4-Chlorophenyl)-4-hydroxy-3-methyldihydrofuran-2(3H)-one (16)

To a solution of olefin 10 (24 mg, 0.10 mmol, 1 equiv) in THF/H$_2$O (4:1, 1 mL) was added K$_2$OsO$_4$ (4.0 mg, 0.010 mmol, 0.1 equiv) and N-methylmorpholine N-oxide (19 mg, 0.16 mmol, 1.6 equiv). The reaction mixture was stirred for 18 h, whereupon the reaction was quenched with sodium sulfite (10 mg, 0.079 mmol, 0.79 equiv) and diluted with water (0.5 mL). The aqueous layer was then extracted with EtOAc (3×5 mL) and the combined organic layers were washed with brine (5 mL), dried over Na$_2$SO$_4$, and concentrated under reduced pressure at 0° C. The crude residue was purified by preparatory TLC (30% acetone/hexanes) to give lactone 16 as a colorless oil (19 mg, 82% yield, 1:1 dr): $[\alpha]_D^{25}$-115.6 (c 0.5, CHCl$_3$); $^1$H NMR (400 MHz, CDCl$_3$) δ 7.43-7.26 (m, 4H), 4.58 (dd, J=4.4, 2.8 Hz, 0.5H), 4.54 (dd, J=10.2, 4.5 Hz, 0.5H), 4.35-4.31 (m, 0.5H), 4.28-4.20 (m, 1H), 4.16 (dd, J=10.1, 2.8 Hz, 0.5H), 1.66 (s, 1.5H), 1.57 (s, 1.5H); $^{13}$C NMR (101 MHz, CDCl$_3$) δ 178.4, 178.1, 138.4, 134.4, 134.0, 133.9, 129.6, 129.4, 129.3, 127.8, 76.5, 76.2, 71.8, 71.6, 53.2, 52.8, 22.3, 18.5; IR (Neat Film, NaCl) 3448, 2976, 2929, 1761, 1496, 1384, 1218, 1178, 1096, 1072, 1014, 982, 927, 737, 688 cm$^{-1}$; HRMS (FAB+) m/z calc'd for C$_{11}$H$_{12}$O$_3$Cl [M+H]$^+$: 227.0475, found 227.0481.

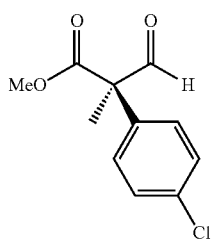

Methyl (R)-2-(4-chlorophenyl)-2-methyl-3-oxopropanoate (17)

A solution of olefin 10 (10 mg, 0.045 mmol, 1 equiv) and NaHCO$_3$ (1.0 mg, 0.011 mmol, 0.25 equiv) in MeOH/CH$_2$Cl$_2$ (1:5, 2.6 mL) was cooled to −78° C. Ozone was bubbled through the reaction mixture for 0.5 h, whereupon the reaction mixture was sparged with N$_2$ and dimethyl sulfide (0.10 mL, 0.14 mmol, 3 equiv) was added. The cooling bath was then removed and the reaction was stirred for 18 h at ambient temperature. The reaction mixture was concentrated under reduced pressure at 0° C. and the crude residue was purified by preparatory TLC (17% Et$_2$O/hexanes) to afford aldehyde 17 as a colorless oil (5.0 mg, 50% yield): [α]$_D^{25}$+9.1 (c 0.07, CHCl$_3$); $^1$H NMR (400 MHz, CDCl$_3$) δ 9.83 (s, 1H), 7.41-7.33 (m, 2H), 7.22-7.13 (m, 2H), 3.81 (s, 3H), 1.69 (s, 3H); $^{13}$C NMR (101 MHz, CDCl$_3$) δ 196.2, 171.8, 134.8, 134.5, 129.5, 128.5, 61.7, 53.1, 18.0; IR (Neat Film, NaCl) 2992, 2954, 2845, 2726, 1721, 1596, 1494, 1455, 1252, 1122, 1096, 1013, 911, 823, 758, 718 cm$^{-1}$; HRMS (FAB+) m/z calc'd for C$_{11}$H$_{12}$ClO$_3$ [M+H]$^+$: 227.0475, found 227.0479.

Crystal Structure Data for Carboxylic Acid 7h

Carboxylic acid 7h was recrystallized by slow evaporation of CH$_2$Cl$_2$ to provide crystals suitable for X-ray analysis.

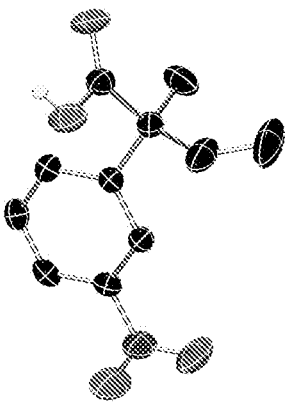

TABLE 6

Crystal data and structure refinement for 7h.

| | |
|---|---|
| Empirical formula | C11 H11 N O4 |
| Formula weight | 221.21 |
| Temperature | 200(2) K |
| Wavelength | 1.54178 Å |
| Crystal system | Monoclinic |
| Space group | P2$_1$ |
| Unit cell dimensions | a = 7.3561(3) Å, a = 90°. |
| | b = 6.7600(3) Å, b = 94.5940(10)°. |
| | c = 10.9461(5) Å, g = 90°. |
| Volume | 542.57(4) Å$^3$ |
| Z | 2 |
| Density (calculated) | 1.354 Mg/m$^3$ |
| Absorption coefficient | 0.879 mm$^{-1}$ |
| F(000) | 232 |
| Theta range for data collection | 4.051 to 72.406°. |
| Index ranges | −9 <= h <= 9, −8 <= k <= 8, −13 <= l <= 13 |
| Reflections collected | 24109 |
| Independent reflections | 2132 [R(int) = 0.0427] |
| Completeness to theta = 67.679° | 100.0% |
| Absorption correction | Semi-empirical from equivalents |
| Refinement method | Full-matrix least-squares on F$^2$ |
| Data/restraints/parameters | 2132/1/146 |
| Goodness-of-fit on F$^2$ | 1.315 |
| Final R indices [I > 2sigma(I)] | R1 = 0.0495, wR2 = 0.1336 |
| R indices (all data) | R1 = 0.0497, wR2 = 0.1346 |
| Absolute structure parameter | 0.08(5) |
| Extinction coefficient | n/a |
| Largest diff. peak and hole | 0.312 and −0.539 e · Å$^{-3}$ |

TABLE 7

Atomic coordinates (×10$^4$) and equivalent isotropic displacement parameters (Å$^2$ × 10$^3$) for 7h. U(eq) is defined as one third of the trace of the orthogonalized U$^{ij}$ tensor.

| | x | y | z | U(eq) |
|---|---|---|---|---|
| C(1) | 6927(3) | 5263(3) | 4602(2) | 32(1) |
| C(2) | 7734(2) | 5232(3) | 5795(2) | 30(1) |
| C(3) | 6640(2) | 5267(3) | 6762(2) | 27(1) |
| C(4) | 4752(2) | 5328(3) | 6510(2) | 33(1) |
| C(5) | 3969(3) | 5364(3) | 5309(2) | 35(1) |
| C(6) | 5062(3) | 5332(3) | 4329(2) | 34(1) |
| C(7) | 7495(2) | 5394(3) | 8089(2) | 33(1) |
| C(8) | 7573(4) | 7595(4) | 8448(2) | 52(1) |
| C(9) | 9331(3) | 4360(5) | 8210(2) | 51(1) |
| C(10) | 10884(3) | 5180(9) | 8624(2) | 86(2) |
| C(11) | 6291(2) | 4290(3) | 8935(2) | 33(1) |
| O(1) | 6125(2) | 2390(3) | 8666(1) | 46(1) |
| O(2) | 5572(2) | 5042(3) | 9776(1) | 49(1) |
| N(1) | 8117(3) | 5216(4) | 3590(2) | 47(1) |
| O(3) | 9753(2) | 5210(6) | 3825(2) | 84(1) |
| O(4) | 7426(3) | 5157(6) | 2546(2) | 81(1) |

TABLE 8

Bond lengths [Å] and angles [°] for 7h.

| | |
|---|---|
| C(1)—C(6) | 1.381(3) |
| C(1)—C(2) | 1.390(2) |
| C(1)—N(1) | 1.466(3) |
| C(2)—C(3) | 1.380(2) |
| C(3)—C(4) | 1.395(2) |
| C(3)—C(7) | 1.538(2) |
| C(4)—C(5) | 1.392(3) |
| C(5)—C(6) | 1.391(3) |
| C(7)—C(9) | 1.517(3) |
| C(7)—C(11) | 1.527(2) |
| C(7)—C(8) | 1.539(3) |
| C(9)—C(10) | 1.318(4) |
| C(11)—O(2) | 1.210(2) |
| C(11)—O(1) | 1.321(3) |
| N(1)—O(3) | 1.210(3) |
| N(1)—O(4) | 1.214(3) |
| C(6)—C(1)—C(2) | 123.08(18) |
| C(6)—C(1)—N(1) | 118.68(17) |
| C(2)—C(1)—N(1) | 118.25(17) |
| C(3)—C(2)—C(1) | 119.26(16) |

TABLE 8-continued

Bond lengths [Å] and angles [°] for 7h.

| | |
|---|---|
| C(2)—C(3)—C(4) | 118.74(16) |
| C(2)—C(3)—C(7) | 120.38(14) |
| C(4)—C(3)—C(7) | 120.72(15) |
| C(5)—C(4)—C(3) | 121.17(17) |
| C(6)—C(5)—C(4) | 120.45(17) |
| C(1)—C(6)—C(5) | 117.31(17) |
| C(9)—C(7)—C(11) | 106.08(18) |
| C(9)—C(7)—C(3) | 110.51(16) |
| C(11)—C(7)—C(3) | 109.42(14) |
| C(9)—C(7)—C(8) | 114.1(2) |
| C(11)—C(7)—C(8) | 109.22(15) |
| C(3)—C(7)—C(8) | 107.45(17) |
| C(10)—C(9)—C(7) | 125.3(4) |
| O(2)—C(11)—O(1) | 122.7(2) |
| O(2)—C(11)—C(7) | 124.49(19) |
| O(1)—C(11)—C(7) | 112.85(17) |
| O(3)—N(1)—O(4) | 122.26(19) |
| O(3)—N(1)—C(1) | 118.91(17) |
| O(4)—N(1)—C(1) | 118.82(19) |

TABLE 9

Anisotropic displacement parameters (Å² × 10³) for 7h. The anisotropic displacement factor exponent takes the form: $-2p^2[h^2 a^{*2}U^{11} + \ldots + 2 h k a^* b^* U^{12}]$

| | $U^{11}$ | $U^{22}$ | $U^{33}$ | $U^{23}$ | $U^{13}$ | $U^{12}$ |
|---|---|---|---|---|---|---|
| C(1) | 38(1) | 32(1) | 26(1) | −1(1) | 2(1) | 1(1) |
| C(2) | 29(1) | 34(1) | 28(1) | 0(1) | 1(1) | 0(1) |
| C(3) | 30(1) | 25(1) | 27(1) | 1(1) | 1(1) | −1(1) |
| C(4) | 30(1) | 34(1) | 35(1) | 1(1) | 4(1) | 1(1) |
| C(5) | 29(1) | 34(1) | 41(1) | 3(1) | −5(1) | −1(1) |
| C(6) | 40(1) | 28(1) | 32(1) | −2(1) | −8(1) | 1(1) |
| C(7) | 31(1) | 42(1) | 26(1) | 0(1) | 3(1) | −4(1) |
| C(8) | 72(2) | 48(1) | 36(1) | −7(1) | 6(1) | −24(1) |
| C(9) | 33(1) | 91(2) | 30(1) | 16(1) | 4(1) | 5(1) |
| C(10) | 32(1) | 176(5) | 49(1) | 35(2) | −6(1) | −14(2) |
| C(11) | 33(1) | 39(1) | 26(1) | 2(1) | 1(1) | 2(1) |
| O(1) | 62(1) | 37(1) | 42(1) | 0(1) | 22(1) | −4(1) |
| O(2) | 60(1) | 51(1) | 38(1) | −7(1) | 22(1) | 5(1) |
| N(1) | 50(1) | 67(1) | 26(1) | 2(1) | 4(1) | 5(1) |
| O(3) | 40(1) | 176(3) | 36(1) | 0(1) | 9(1) | 5(1) |
| O(4) | 66(1) | 151(3) | 25(1) | −7(1) | −1(1) | 12(1) |

TABLE 10

Hydrogen coordinates (×10⁴) and isotropic displacement parameters (Å² × 10³) for 7h.

| | x | y | z | U(eq) |
|---|---|---|---|---|
| H(2) | 9023 | 5188 | 5942 | 36 |
| H(4) | 3987 | 5347 | 7168 | 40 |
| H(5) | 2680 | 5410 | 5158 | 42 |
| H(6) | 4546 | 5355 | 3505 | 40 |
| H(8A) | 8291 | 8322 | 7880 | 78 |
| H(8B) | 8145 | 7730 | 9284 | 78 |
| H(8C) | 6333 | 8135 | 8410 | 78 |
| H(9) | 9363 | 3012 | 7967 | 62 |
| H(10A) | 10911 | 6525 | 8877 | 103 |
| H(10B) | 11978 | 4427 | 8671 | 103 |
| H(1) | 5466 | 1842 | 9160 | 69 |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:
1. A method for preparing a compound of formula (I):

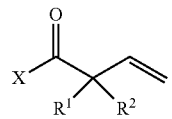

or a salt thereof,
comprising
treating a compound of formula (II):

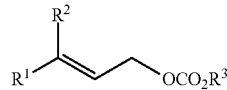

or a salt thereof,
with a masked acyl cyanide (MAC) nucleophile and an iridium catalyst under alkylation conditions, to provide a compound of formula (Ia):

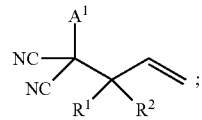

and
treating the compound of Formula (Ia) with an amine, an alcohol, or an acid in the presence of water, to provide the compound of Formula (I);
wherein, as valence and stability permit,
$A^1$ is —OH or any protecting group;
X is OH, $OR^4$, or $NR^aR^b$;
$R^1$ and $R^2$ are each independently substituted or unsubstituted alkyl, haloalkyl, alkenyl, alkynyl, aralkyl, cycloalkyl, aryl, heteroaralkyl, heteroaryl, (cycloalkyl)alkyl, cycloalkyl, (heterocycloalkyl)alkyl, or heterocycloalkyl;
$R^3$ is substituted or unsubstituted alkyl;
$R^4$ is substituted or unsubstituted alkyl, alkenyl, haloalkyl, (cycloalkyl)alkyl, or cycloalkyl; and
$R^a$ and $R^b$ are each independently hydrogen or substituted or unsubstituted alkyl, alkenyl, alkynyl, aralkyl, cycloalkyl, aryl, heteroaralkyl, heteroaryl, (cycloalkyl)alkyl, cycloalkyl, (heterocycloalkyl)alkyl, or heterocycloalkyl; or $R^a$ and $R^b$, together with the nitrogen atom to which they are attached, form a 5- or 6-membered heterocycloalkyl.

2. A method for preparing a compound of formula (Ia):

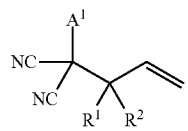
(Ia)

or a salt thereof,
comprising treating a compound of formula (II):

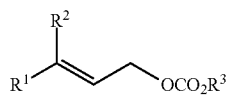
(II)

or a salt thereof,
with a masked acyl cyanide (MAC) nucleophile and an iridium catalyst under alkylation conditions,
wherein, as valence and stability permit,
$A^1$ is —OH or any protecting group;
$R^1$ and $R^2$ are each independently substituted or unsubstituted alkyl, haloalkyl, alkenyl, alkynyl, aralkyl, cycloalkyl, aryl, heteroaralkyl, heteroaryl, (cycloalkyl)alkyl, cycloalkyl, (heterocycloalkyl)alkyl, or heterocycloalkyl;
$R^3$ is substituted or unsubstituted alkyl.

3. The method of claim 2, wherein the method further comprises treating the compound of formula (Ia) with acid in the presence of water to provide a compound of formula (I):

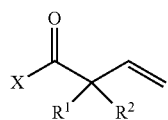
(I)

or salt thereof,
wherein X is OH.

4. The method of claim 2, wherein the method further comprises treating the compound of formula (Ia) with an alcohol to provide a compound of formula (I):

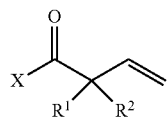
(I)

or salt thereof,
wherein X is $OR^4$; and
$R^4$ is substituted or unsubstituted alkyl, alkenyl, haloalkyl, (cycloalkyl)alkyl, or cycloalkyl.

5. The method of claim 2, wherein the method further comprises treating the compound of formula (Ia) with an amine to provide a compound of formula (I):

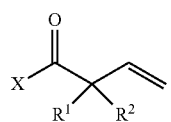
(I)

or salt thereof,
wherein X is $NR^aR^b$; and
$R^a$ and $R^b$ are each independently hydrogen or substituted or unsubstituted alkyl, alkenyl, alkynyl, aralkyl, cycloalkyl, aryl, heteroaralkyl, heteroaryl, (cycloalkyl)alkyl, cycloalkyl, (heterocycloalkyl)alkyl, or heterocycloalkyl; or
$R^a$ and $R^b$, together with the nitrogen atom to which they are attached, form a substituted or unsubstituted 5- or 6-membered heterocycloalkyl.

6. The method of claim 1, wherein the masked acyl cyanide (MAC) nucleophile have a structure according to formula (A):

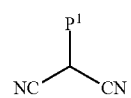
(A)

wherein $P^1$ is any protecting group that is stable to the reaction conditions.

7. The method of claim 1, wherein the iridium catalyst is used in an amount from about 0.01 mol % to about 10 mol % relative to the compound of formula (II).

8. The method of claim 1, wherein the iridium catalyst is prepared by combining an iridium source and a chiral ligand.

9. The method of claim 8, wherein the iridium source is selected from (acetylacetonato)(1,5-cyclooctadiene)iridium(I), (acetylacetonato)(1,5-cyclooctadiene)iridium(I), (acetylacetonato)dicarbonyliridium(I), bis[1,2-bis(diphenylphosphino)ethane]carbonyl chloroiridium(I), bis(1,5-cyclooctadiene)diiridium(I) dichloride, bis(1,5-cyclooctadiene)iridium(I) tetrafluoroborate, bis(cyclooctadiene)iridium(I) tetrakis(3,5-bis(trifluoromethyl)phenyl)borate, chlorobis(cyclooctene)iridium(I)dimer, (1,5-cyclooctadiene)bis(methyldiphenylphosphine)iridium(I) hexafluorophosphate, (1,5-cyclooctadiene)(hexafluoroacetylacetonato)iridium(I), (1,5-cyclooctadiene)-η5-indenyl)iridium(I), (1,5-cyclooctadiene)(methoxy)iridium(I) dimer, (1,5-cyclooctadiene)(pyridine)(tricyclohexylphosphine)-iridium(I) hexafluorophosphate, (1,5-cyclooctadiene)(pyridine)(tricyclohexylphosphine)-iridium(I) hexafluorophosphate, and (1,5-cyclooctadiene)(pyridine)(tricyclohexylphosphine)iridium(I) tetrakis[3,5-bis(trifluoromethyl)phenyl]borate.

10. The method of claim 8, wherein the chiral ligand is an enantioenriched phosphine ligand.

11. The method of claim 10, wherein the enantioenriched phosphine ligand is a phosphoramidite ligand.

12. The method of claim 8, wherein the chiral ligand is used in an amount from about 0.1 mol % to about 100 mol % relative to the compound of formula (II).

13. The method of claim 1, wherein the method further comprises preparing a mixture of the iridium catalyst and an additive.

14. The method of claim 13, wherein the additive is a Lewis acid.

15. The method of claim 13, wherein the additive is used in an amount from about 1 mol % to about 1000 mol % relative to the compound of formula (II).

16. The method of claim 13, wherein the mixture further comprises a base.

17. The method of claim 16, wherein the base is used in an amount of about 0.1 mol % to about 100 mol % relative to the compound of formula (II).

18. The method of claim 1, wherein the alkylation conditions include reaction in methyl tert-butyl ether, toluene, or tetrahydrofuran.

19. The method of claim 1, wherein $A^1$ is a protecting group selected from methoxymethyl ether, ethoxymethyl ether, trifluoroethyl ether, and benzyl ether.

20. The method of claim 1, wherein $R^3$ is substituted or unsubstituted lower alkyl.

21. The method of claim 2, wherein $A^1$ is a protecting group selected from methoxymethyl ether, ethoxymethyl ether, trifluoroethyl ether, and benzyl ether.

22. The method of claim 2, wherein $R^3$ is unsubstituted lower alkyl.

23. A method of synthesizing a pharmaceutical agent, comprising preparing a compound of formula (I) according to any one of claims 1, 3-5, 6, 7, 8, 9, 10, 11, 12, 13, 14, 15, 16, 17, 18, 19, and 20; and synthesizing the pharmaceutical agent from the compound of formula (I).

* * * * *